(12) United States Patent
Inglese et al.

(10) Patent No.: US 11,903,752 B2
(45) Date of Patent: Feb. 20, 2024

(54) DENTAL CHAIR-SIDE TOMOSYNTHESIS SYSTEM

(71) Applicant: CARESTREAM DENTAL TECHNOLOGY TOPCO LIMITED, London (GB)

(72) Inventors: Jean-Marc Inglese, Bussy-Saint-Georges (FR); Edward Shellard, Atlanta, GA (US); Jay Schildkraut, Rochester, NY (US); Krishnamoorthy Subramanyan, Brighton, NY (US); Victor Wong, Pittsford, NY (US)

(*) Notice: Subject to any disclaimer, the term of this patent is extended or adjusted under 35 U.S.C. 154(b) by 773 days.

(21) Appl. No.: 16/640,872

(22) PCT Filed: Aug. 21, 2018

(86) PCT No.: PCT/EP2018/072589
§ 371 (c)(1),
(2) Date: Feb. 21, 2020

(87) PCT Pub. No.: WO2019/038304
PCT Pub. Date: Feb. 28, 2019

(65) Prior Publication Data
US 2020/0352530 A1 Nov. 12, 2020

Related U.S. Application Data

(63) Continuation of application No. PCT/US2017/048169, filed on Aug. 23, 2017.

(51) Int. Cl.
*A61B 6/00* (2006.01)
*A61B 6/14* (2006.01)
(Continued)

(52) U.S. Cl.
CPC ............ *A61B 6/145* (2013.01); *A61B 5/0066* (2013.01); *A61B 6/025* (2013.01); *A61B 6/06* (2013.01); *A61B 6/4417* (2013.01); *A61B 6/547* (2013.01); *A61B 6/584* (2013.01); *A61L 31/026* (2013.01); *A61L 31/18* (2013.01); *A61B 6/4007* (2013.01);
(Continued)

(58) Field of Classification Search
CPC ...................... A61B 2090/3966; A61B 6/145
See application file for complete search history.

(56) References Cited

U.S. PATENT DOCUMENTS

2016/0220212 A1* 8/2016 Duewer .................... G06T 5/50

* cited by examiner

*Primary Examiner* — Dani Fox

(57) ABSTRACT

An intraoral imaging apparatus for tomosynthesis imaging has an x-ray source having a primary collimator that defines boundaries of a radiation field. A transport apparatus translates the x ray source along a path for tomographic imaging. An intraoral x-ray detector defines an imaging area for the radiation field. A positioning apparatus correlates the position of the intraoral detector to the position of a secondary collimator. One or more radio-opaque markers provided on a detector attachment is coupled to the detector, the one or more markers configured to condition acquired x-ray images to relate the spatial position of the intraoral x-ray detector to the x-ray source position, wherein the one or more markers are disposed within the defined imaging area. A control logic processor accepts image data from the detector and determines the relative location of the source with respect to the detector according to detected marker position.

19 Claims, 39 Drawing Sheets

(51) Int. Cl.
*A61B 5/00* (2006.01)
*A61B 6/02* (2006.01)
*A61B 6/06* (2006.01)
*A61L 31/02* (2006.01)
*A61L 31/18* (2006.01)
*A61B 90/00* (2016.01)

(52) U.S. Cl.
CPC ........... *A61B 6/4233* (2013.01); *A61B 6/4435* (2013.01); *A61B 6/4452* (2013.01); *A61B 6/587* (2013.01); *A61B 2090/3966* (2016.02)

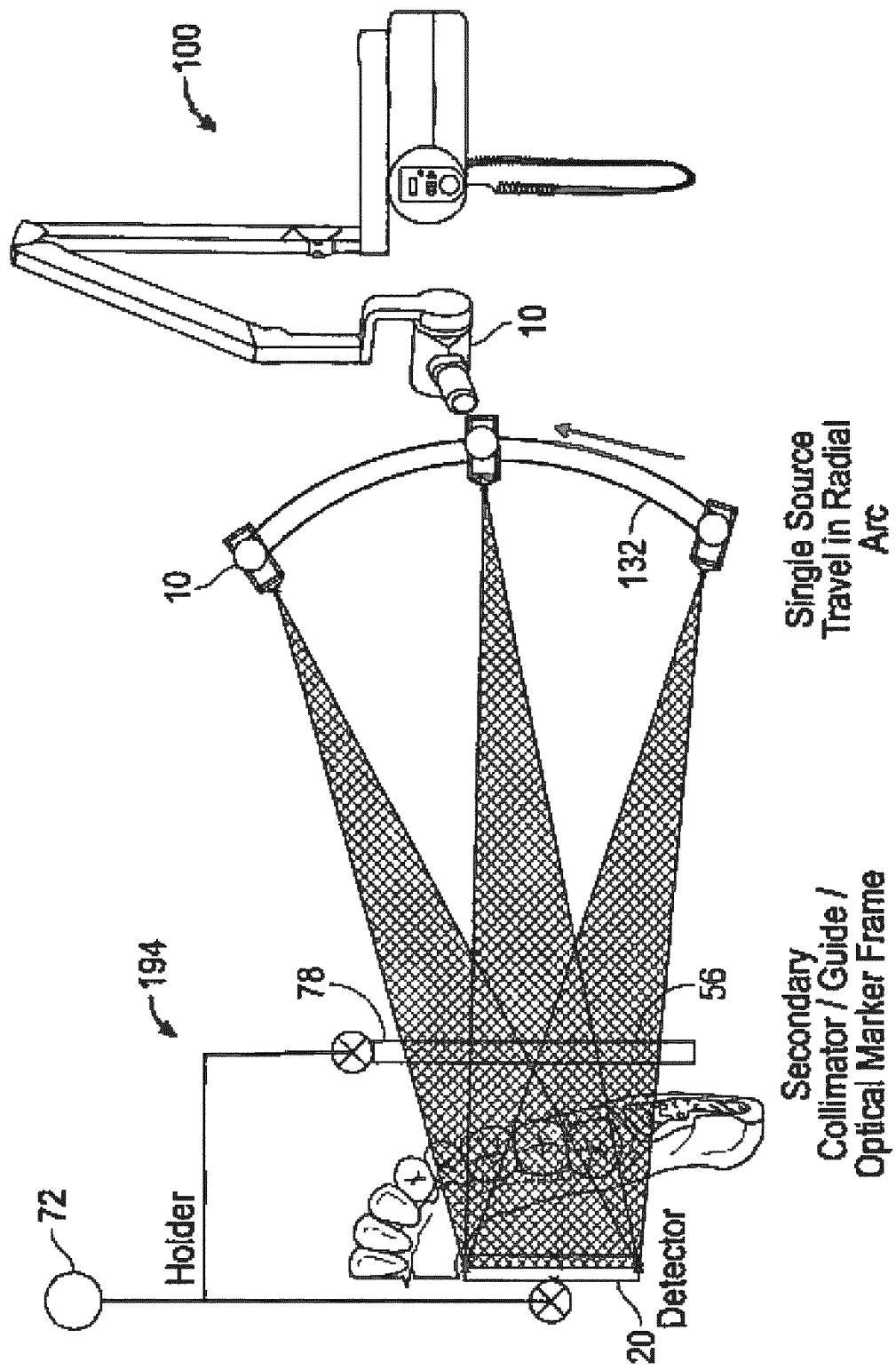

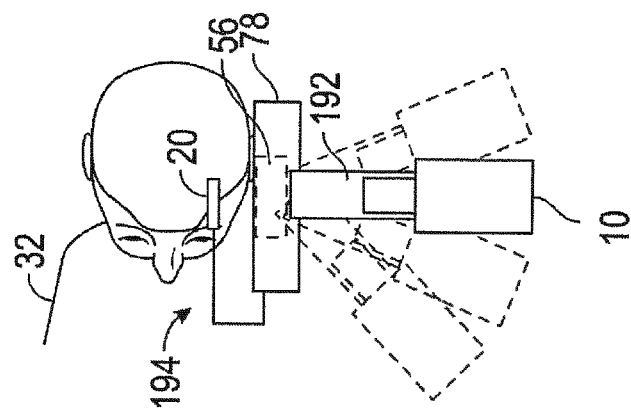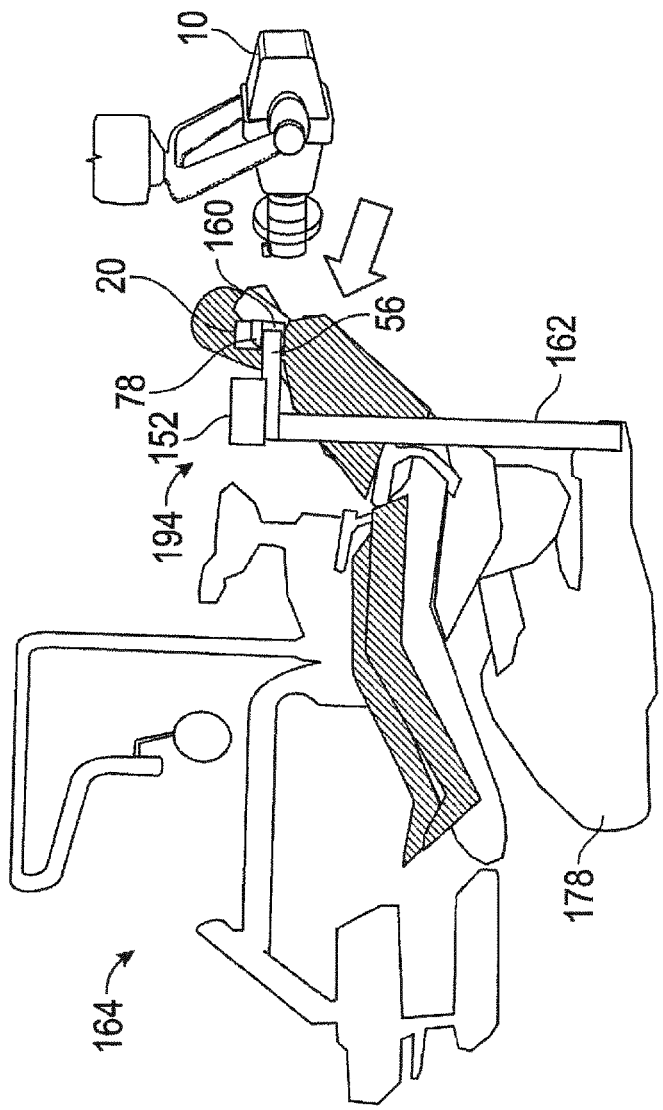
FIG. 13B
FIG. 13A

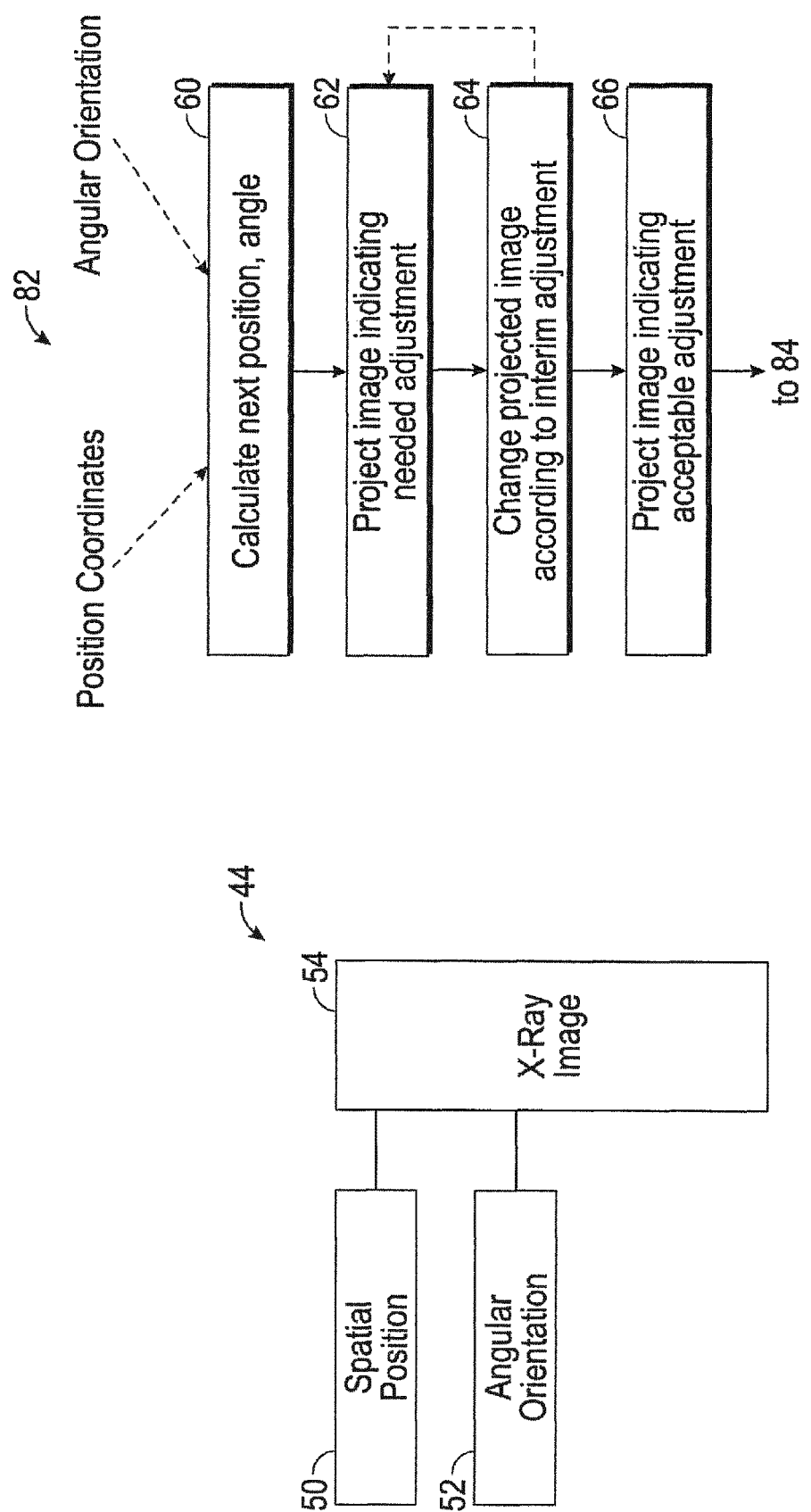

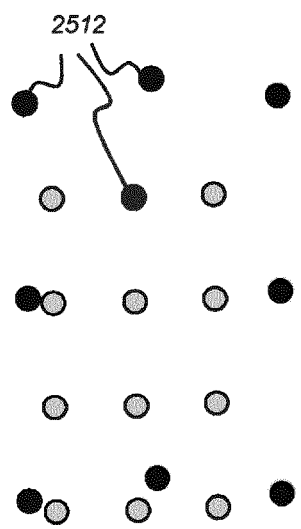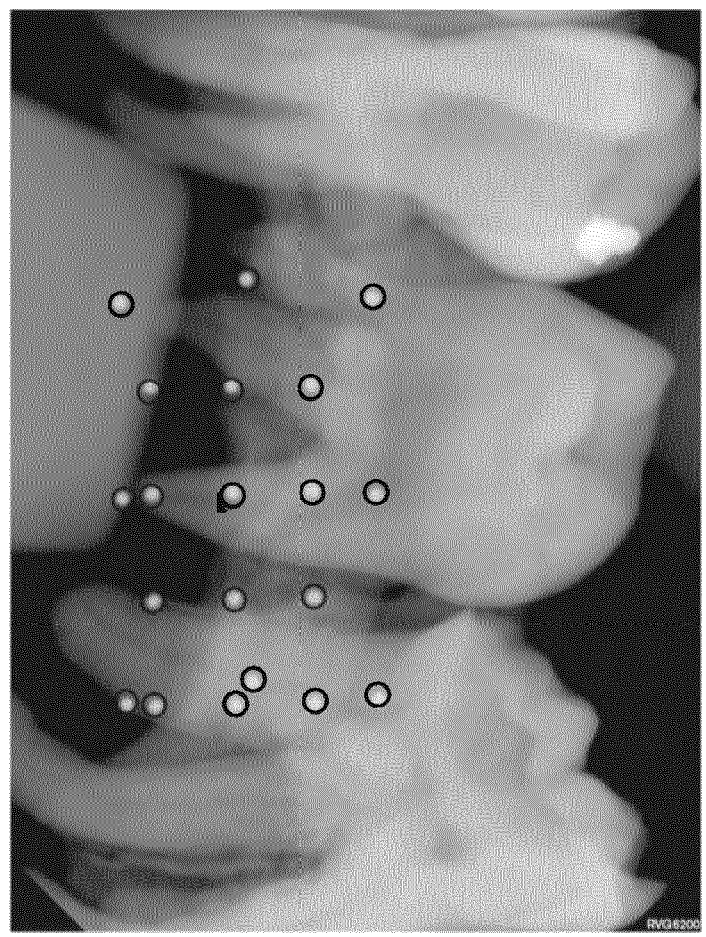
FIG. 27B

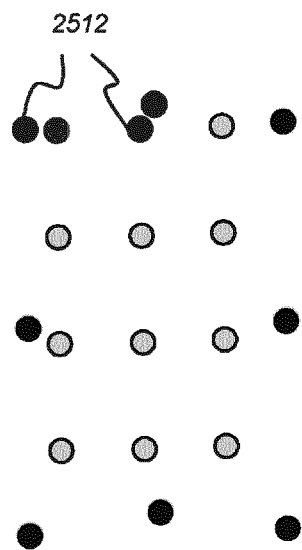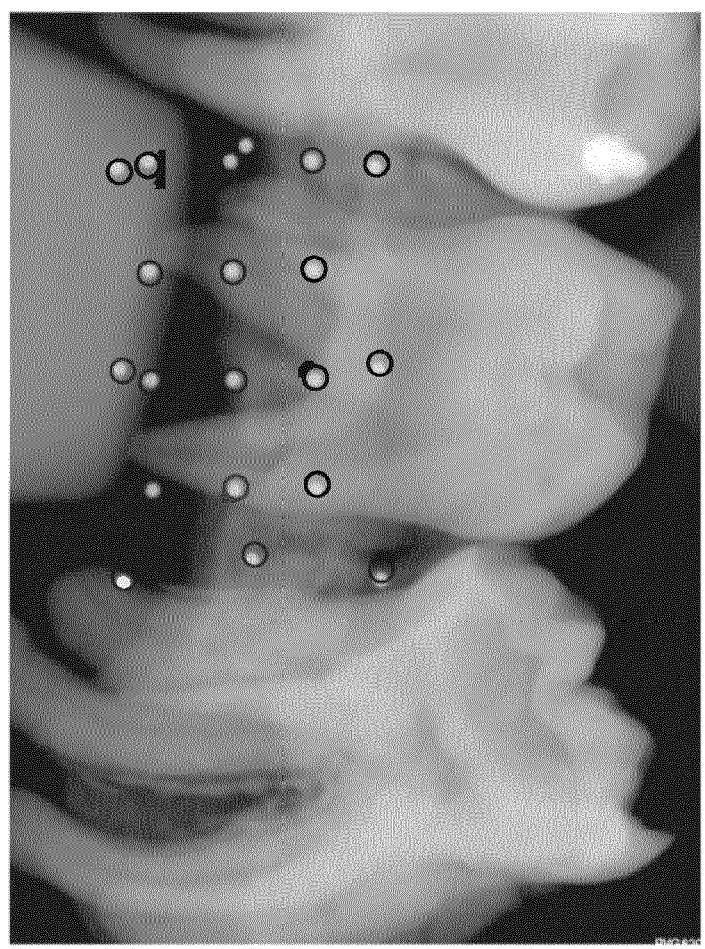
FIG. 27C

DENTAL CHAIR-SIDE TOMOSYNTHESIS SYSTEM

CROSS REFERENCE TO RELATED APPLICATIONS

The present application is a continuation-in-part of earlier-filed application PCT/US17/48169 filed on 22 Aug. 2017.

TECHNICAL FIELD

The disclosure relates generally to intraoral imaging and more particularly relates to methods and apparatus for intraoral tomosynthesis imaging.

BACKGROUND

A 3-dimensional (3-D) or volume x-ray image can be of significant value for diagnosis and treatment of teeth and supporting structures. A volume x-ray image for this purpose is formed by combining image data from two or more individual 2-D projection images, obtained within a short time of each other and with a well-defined angular and positional geometry between each projection image and the subject tooth and between each projection image and the other projection images. Cone-Beam Computed Tomography (CBCT) is one established method for obtaining a volume image of dental structures from multiple projection images. In CBCT imaging, an image detector and a radiation source orbit a subject and obtain a series of x-ray projection images at small angular increments. The information obtained is then used to synthesize a volume image that faithfully represents the imaged subject to within the available resolution of the system, so that the volume image that is formed can then be viewed from any number of angles. Commercially available CBCT apparatus for dental applications include the CS 8100 3D System from Carestream Health, Inc., Rochester, N.

While CBCT imaging is a powerful diagnostic tool, however, there can be cases where, even though volume imaging is beneficial, the full-fledged capability of CBCT imaging is not needed. This has been acknowledged, for example, in disclosures of U.S. Patent Application Publication No. 2007/0127801 entitled "Method for Limited Angle Tomography" by Kalke and U.S. Pat. No. 7,269,241 entitled "Method and Arrangement for Medical X-ray Imaging and Reconstruction from Sparse Data" to Siltanen et al. For some types of volume imaging, such as for use in guiding implant placement, for example, a rudimentary volume imaging capability would be useful. Volume imaging can also help to avoid superposition anomalies between adjacent dental structures. For uses such as these, numerous x-ray projection images, such as those provided from a CBCT system would not be required. Instead, sufficient volume information can be obtained using a smaller number of x-ray images, provided a spatial coordinate reference between images is maintained.

As a general principle, it would be advantageous to obtain the minimum number of x-ray exposures needed in order to generate the volume diagnostic data. A complete CBCT series of projection images acquired over a 180 degree orbit requires higher cumulative radiation dosage than does a partial series that is either taken over a smaller range of angles or uses fewer projection images taken at increased relative angular increments. Thus, the methods taught in the '7801 Kalke and '241 Siltanen et al. disclosures cited previously can help to reduce patient exposure where full CBCT imaging is not needed.

Tomosynthesis appears to offer the dental practitioner a number of advantages over conventional 2D radiography and 3D tomography imaging, such as CBCT imaging, of intraoral features. In tomosynthesis, as with other volume imaging approaches, a limited number of 2D projection images are obtained in sequence, with each image frame shifted in terms of relative angle from the previously acquired image frame. Reconstruction techniques can then be used to form a volume image of sufficient depth and resolution for a number of diagnosis and assessment functions. This gives tomosynthesis some of the benefits of full-scale tomography imaging for providing volume data, but at lower dose than tomography requires.

Tomosynthesis imaging employs incremental geometric change of the relative radiation source angle, at each image, with respect to the detector surface. Conventional tomosynthesis systems, such as those used for mammography, for example, have inherent control of source position relative to detector and thus automatically achieve geometric alignment, which applies from one imaging exam to the next. With intraoral imaging, however, such types of mechanically fixed geometry are not easily obtainable. The intraoral detector is largely hidden from view and must be flexibly positionable at various locations within the mouth, frustrating attempts at straightforward source-to-detector alignment. Not only should the system be able to positively identify the boundary geometry of the detector outline, but the path traced by the partial orbit of the source should be symmetrical to detector pixel row/column geometry.

Related difficulties for intraoral tomosynthesis include the need for accurate collimation of the radiation beam. Effective collimation helps to prevent unnecessary exposure of areas that lie beyond boundaries of the detector.

Still other aspects of the intraoral tomosynthesis system relate to the need to represent the reconstructed tomosynthesis image in suitable format for ease of use in assisting diagnosis.

Thus, although a number of solutions have been proposed for providing intraoral tomosynthesis, there remain considerable areas for improvement in making tomosynthesis technology suitable for the dental practitioner.

Reference is hereby made to the following:
US 2015/0359504 entitled "Intraoral Tomosynthesis Systems, Methods, and Computer-Readable Media for Dental Imaging" by Zhou et al.;
U.S. Pat. No. 8,670,521 entitled "Method for Generating an Intraoral Volume Image" by Bothorel et al., commonly assigned;
U.S. Pat. No. 5,828,722 entitled "X-ray Diagnostic Apparatus for Tomosynthesis Having a Detector that Detects Positional Relationships" by Ploetz et al.;
U.S. Pat. No. 5,629,972 entitled "Intraoral Radiograph Alignment Device" to Hausmann et al.;
U.S. Pat. No. 9,332,951 entitled "Alignment Apparatus for Dental Intraoral Radiology" to Inglese et al.;
US 2016/0220212 entitled "Methods, Systems, Apparatuses, and Computer Programs for Removing Artifacts from a Tomosynthesis Dataset" by Duewer;
US 2016/0317107 entitled "Digital Tomosynthesis Systems, Methods, and Computer Readable Media for Intraoral Dental Tomosynthesis Image" by Zhou et al.;
U.S. Pat. No. 5,598,454 entitled "X-ray Diagnostics Installation" to Franetzki et al.

SUMMARY

An object of the present invention is to advance the art of intraoral radiography by providing exemplary apparatus and/or method embodiments for generating a volume image from a small number of x-ray images obtained by an intraoral imaging detector.

Another object of this application is to address, in whole or in part, at least the foregoing and other deficiencies in the related art.

It is another object of this application to provide, in whole or in part, at least the advantages described herein.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to one aspect of the disclosure, there is provided an intraoral imaging apparatus that can include a) an x-ray source having a primary collimator that defines boundaries of a radiation field, b) an intraoral x-ray detector, c) a secondary collimator that is coupled to the intraoral imaging apparatus at a collimator position, d) a positioning apparatus that correlates the position of the detector to the position of the secondary collimator, e) one or more markers that relate the spatial position of the intraoral x-ray detector to the x-ray source position, and f) a control logic processor that accepts image data from the detector and determines the relative location of the source with respect to the detector according to detected marker position.

According to another aspect of the present disclosure, there is provided an intraoral imaging apparatus for tomosynthesis imaging comprising: a) an x-ray source having a primary collimator that defines boundaries of a radiation field; b) a transport apparatus that translates the x ray source along a path for tomographic imaging; c) an intraoral x-ray detector that defines an imaging area for the radiation field; d) a positioning apparatus that correlates the position of the intraoral detector to the position of a secondary collimator; e) one or more radio-opaque markers provided on a detector attachment that is coupled to the detector, the one or more markers configured to condition acquired x-ray images to relate the spatial position of the intraoral x-ray detector to the x-ray source position, wherein the one or more markers are disposed within the defined imaging area; and f) a control logic processor that accepts image data from the detector and determines the relative location of the source with respect to the detector according to detected marker position.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 10A is a schematic diagram that shows an intraoral imaging apparatus for tomosynthesis imaging with the x-ray source transported along an arcuate track.

FIG. 13A shows a treatment system with chair and other apparatus for dental procedures.

FIG. 13B is a top view schematic that shows an arrangement with the x-ray source coupled to the collimator, chair, floor, or other equipment.

FIG. 21 is a block diagram showing spatial position and angular orientation information associated with the image data.

FIG. 22 is a logic flow diagram that shows system activity in preparation for each image capture in a sequence.

FIGS. 27A, 27B, and 27C show selected 2D projection images of a few representative teeth from a tomosynthesis series using markers 2512 arranged in two layers.

DESCRIPTION OF EXEMPLARY EMBODIMENTS

Figure 1:
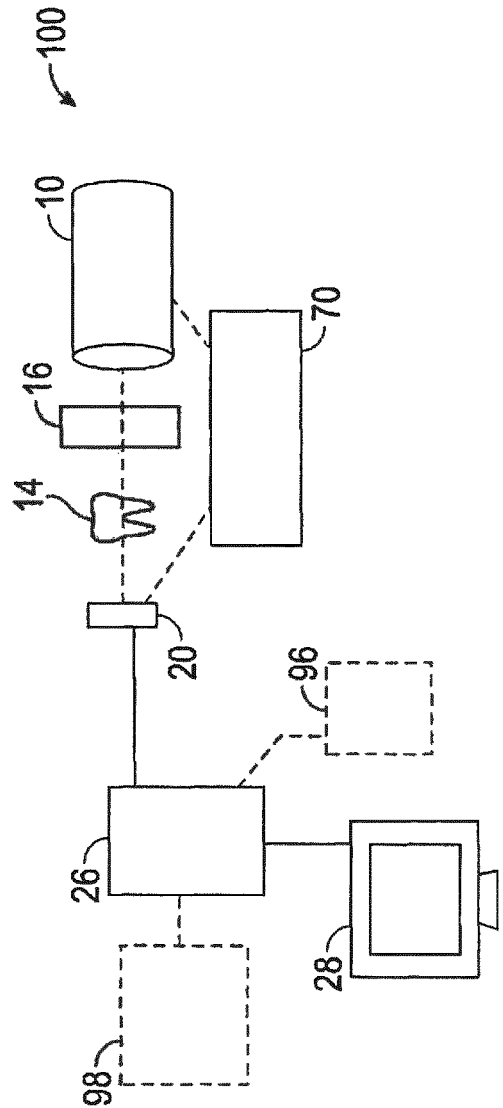
FIG. 1 is a schematic diagram showing components of a chairside tomosynthesis imaging apparatus according to an exemplary embodiment according to the application.

The following is a detailed description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a camera or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the present disclosure, the term "detector" refers to the element that is placed in the patient's mouth, receives radiation, and provides the image content. Such a detector is a digital detector that provides the x-ray image data directly to an imaging system.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2-D images of pixels, taken at different relative angles, then combining the image data to form corresponding 3-D voxels. For the purposes of the description herein, the terms voxel and pixel can generally be considered equivalent, describing an image elemental datum that is capable of having a range of numerical values. Voxels and pixels have the attributes of both spatial location and image data code value.

Planes can be considered "in parallel" if they are parallel to within no more than 12 degrees in any direction.

FIG. 1 is a schematic diagram showing components of an exemplary chairside tomosynthesis imaging apparatus 100 according to certain exemplary method and/or apparatus embodiments of the present disclosure. An x-ray source 10 directs radiant energy through a subject tooth 14 or other feature toward an intraoral detector 20, over a range of angles. A collimator 16 conditions the angular extent of source 10 radiation so that the exposure is constrained to within the region of interest. An alignment apparatus 70 senses and optionally controls the alignment of the radiation field from source 10 and through collimator 16 to provide radiation over the region of interest. Intraoral detector 20 is in signal communication with a control logic processor 26 that acquires and processes the image content to provide a tomosynthesis image on a display 28. Tomosynthesis imaging requires a changing relative angle of the source 10 to the detector 20, as described in more detail herein. Control logic processor 26 provides the control required for tomosynthesis image acquisition.

Tomosynthesis imaging requires that the components shown in FIG. 1 acquire two or more 2D projection images of the region of interest, such as images of one or more adjacent teeth, for example. The generated image content includes some amount of contour and depth information, but not the more geometrically complete image volume data obtained from tomography, such as from CBCT systems.

The tomosynthesis data provides a measure of depth information without full volume image content. Tomosynthesis allows generation of slices into the imaged object, wherein the slices are at different depths.

Reflectance Image Acquisition

An optional reflectance imaging apparatus 96 can also be provided as part of some exemplary chairside oral imaging method and/or apparatus embodiments, such as for providing more accurate positioning information for the detector 20 placed within the mouth of the patient. Imaging apparatus 96 can provide contour imaging, such as by projection of a structured light pattern onto the intraoral feature of interest. Contour information is then processed in order to generate a 3D mesh showing surface features. For this purpose, the reflectance imaging camera serves as an optical scanner. Alternately, imaging apparatus 96 can be a 2D camera for obtaining one or more monochromatic or color images from and around the region of interest.

Reflectance imaging can be used, for example, to determine head size and/or orientation. Acquired reflectance images can also serve as an aid to detecting patient motion during tomosynthesis and/or other radiological image acquisition. A contour imaging camera image, such as provided by a CS3600 intraoral scanner from Carestream Dental LLC, can provide more information than 2D reflectance images for guiding and/or correcting the volume reconstruction processing used in tomosynthesis and for motion detection during the tomosynthesis exam.

An optional ultrasound imaging apparatus 98 can similarly be provided as a support system for chairside oral imaging apparatus 100.

According to an alternate exemplary embodiment according to the application, a full-mouth scanning apparatus works in conjunction with the radiographic imaging system. This enables the simultaneous acquisition of both radiographic and reflectance images, for example, which can be useful for subsequent reconstruction processing. The reflectance and tomosynthesis image content can be fused together to show some depth information with reference to highly accurate surface contour information.

Types of imaging apparatus that acquire depth-resolved image content, such as optical coherence tomography (OCT) and ultrasound imaging systems, obtain from captured reflectance signals not only surface contour information, but also potentially provide some amount of additional information for characterization of tissue and features detected, up to some depth below the surface. This type of depth-resolved image content can be a more useful aid to support and validate positioning of the tomosynthesis acquisitions as well as to help identify and report or compensate for detected movement of the patient during the imaging session. There can be supportive information obtained by depth-resolved imaging apparatus for features just beneath the surface, for example, that can be more useful for positioning guidance and verification than is available when only using surface contour imaging content.

Radiation Source

According to exemplary method and/or apparatus embodiments of the present disclosure, the x-ray source 10 is a Spindt-type field emitter (including carbon nanotube-based field emitters), providing radiant energy from a number of distributed x-ray sources. The x-ray sources can be, for example, a distributed array of Spindt-type field emitters, which can be peripherally arranged about a central thermionic source. The x-ray sources are stationary or relatively fixed in position with respect to each other within the array; the array itself moves as a single unit. This type of x-ray source is capable of rapid on/off switching on the order of microseconds.

Other suitable x-ray sources can include paired pulsed conventional fluoro-capable thermionic sources in an array, where the sources are spatially separated. These options provide sufficient x-ray fluence with short exposure times and simultaneously allow exposure sequences without overheating.

A Spindt-type field emitter based x-ray source has one or more cathodes within a vacuum chamber, wherein each cathode is formed from a large number of individual Spindt-type field emitters that, given excitation current, provide electrons that are then accelerated toward one or more anodes in the chamber.

Alternately, the x-ray source can be a more conventional thermionic source, coupled with a transport apparatus that provides the needed energy to move the x-ray source along a linear or non-linear (e.g., curved) travel path that can be segmented or continuous for directing radiation toward the subject.

According to an exemplary embodiment according to the application, the same x-ray source can be used in any of a set of modes for conventional radiography or 3D imaging. Thus, the same radiation imaging apparatus can be used for acquiring single-shot radiographic images, or for acquiring and processing projection images for tomography including CBCT, tomosynthesis, or for fluoroscopy or radioscopy imaging, as described in more detail herein.

Generator

The radiation generator that is part of the x-ray source can provide pulsed or continuous operation. The generator can provide a single pulse or a series of pulses, with pulse widths varied in order to provide suitable exposure conditions for particular features.

Imaging Detector

The imaging detector exemplary method and/or apparatus embodiments is a small, intraoral digital radiography (DR) detector that acquires image data at a rate sufficient for tomosynthesis imaging. The imaging detector can be any suitable shape and can be rigid or flexible.

Signal communication with the imaging detector can be wired or wireless. The image detector can receive power from a cable or can have an on-board rechargeable battery.

In order to meet the requirements of tomosynthesis imaging, the intraoral detector has a fast response time, with an image acquisition rate sufficient for tomosynthesis acquisition, acquiring at least about 2 frames per second (fps), at least 5 fps, or at least 10 fps.

The imaging detector can be a conventional DR detector that generates image content using relative energy integration or can be a photon counting detector. According to an exemplary embodiment according to the application, the same imaging apparatus can allow connection to multiple types of imaging detector. This allows a versatile imaging apparatus capable of single-frame radiographic imaging (e.g., up to 43×43 cm) with one detector and multiple projection image acquisition (e.g., 3D or volume imaging) using a different detector, for example, in addition to chairside tomosynthesis imaging described herein.

Some of the advantages of the photon counting detection compared to the energy integration detection include: (i) reduction of electrical noise and improvement of the signal-to-noise ratio; and (ii) improvement of image contrast, such as adjusting weighting factors for images acquired with energy binning. Photon counting tomosynthesis can provide improved diagnostic accuracy.

Conventional integrating x-ray sensors are spatially digitized and provide an analog output that represents the accumulated charge received for each pixel during the exposure. High noise levels can be a problem with integrating sensors. In photon counting, each incoming photon generates a charge, and each charge event is recorded. The actual count of photons, or a value correspondingly computed according to the count, is provided as the image data for each pixel. Advantageously, photon counting has high immunity to noise, provided that pulse strength exceeds background noise levels.

Figure 2A:
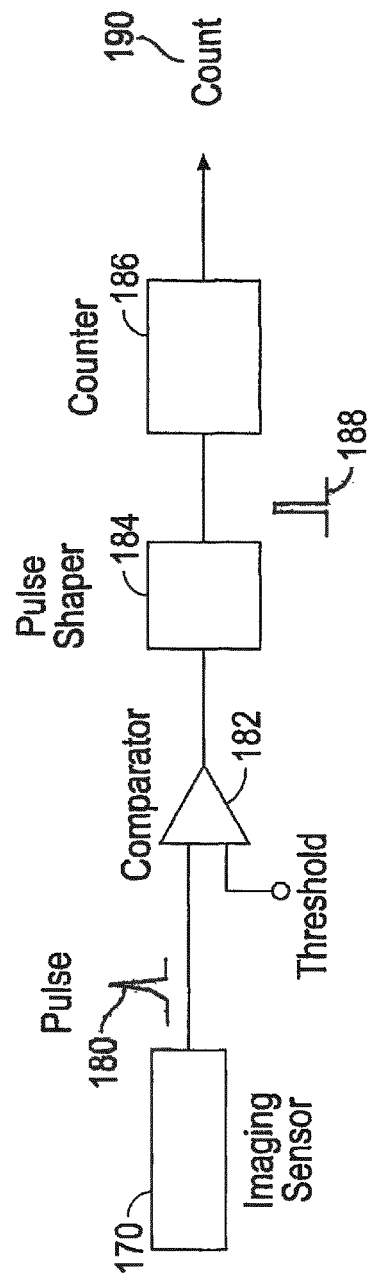
FIG. 2A is a schematic diagram that shows the photon-counting sequence.

FIG. 2A shows the photon-counting sequence in schematic form. An incoming photon generates a pulse 180 at a given energy level. The pulse 180 energy is compared against a threshold value at a comparator 182 and shaped in a pulse shaper 184 to form a shaped pulse 188. A counter 186 then records the pulse event and provides a digital output, a pulse count value 190. A separate pulse count value 190 is obtained for each pixel element in imaging sensor 170 that is used for detector 20. The threshold value can be adjustable or selectable from a range of values, depending on the photon energies of interest. Photon counting x-ray detectors provide suitable performance at low signal level, and therefore allow reducing the x-ray dose given to a patient.

Applicants have recognized that multiple detector technologies can be combined. Exemplary combinations include: (1) Indirect-Detection with Integration, (2) Direct-Detection with Integration, (3) Indirect-Detection with Photon-Counting, and (4) Direct-Detection with Photon-Counting. Indirect-Detection with Integration provides reduced detector cost and scalability. Direct-Detection with Integration provides reduced dose with larger-scale detectors. Indirect-Detection with Photon-Counting provides for reduced dose. Direct-Detection with Photon-Counting can provide reduced dose and/or color x-ray, as described in more detail herein.

A further advantage of pulse counting relates to its capability to count pulses 180 at multiple threshold values. Referring to the schematic diagram of FIG. 2B, two comparators 182a and 182b are shown for measuring pulse energy. In this particular configuration, a comparator 182a, a pulse shaper 184a, and a counter 186a provide a count 190a value for all pulses above a first threshold; similarly, a comparator 182b, a pulse shaper 184b, and a counter 186b account for only pulses above a higher, second threshold and provide a count 190b accordingly. Simple subtraction then identifies the different power levels achieved for each pulse. It can be appreciated that more than two threshold levels can be measured, using a corresponding arrangement of comparator circuitry, allowing pulse counts at any of a number of threshold values. In addition, thresholds can be selectable, such as adjustable to adjust the response of imaging sensor 170 to various photon energy levels. Thus, for example, an operator can use a set of preset thresholds for differentiating softer from denser tissue in the image that is finally generated.

In addition to setting minimum of floor thresholds (e.g., for noise reduction), embodiments of the present invention for multi-spectral x-ray imaging can also provide the option of using additional upper or maximum thresholds for photon energy. This upper threshold capability can be used for a number of functions, including reducing the generation of excessive noise signals such as from metal artifacts or x-rays passing directly through the direct detection material.

Figure 2B:
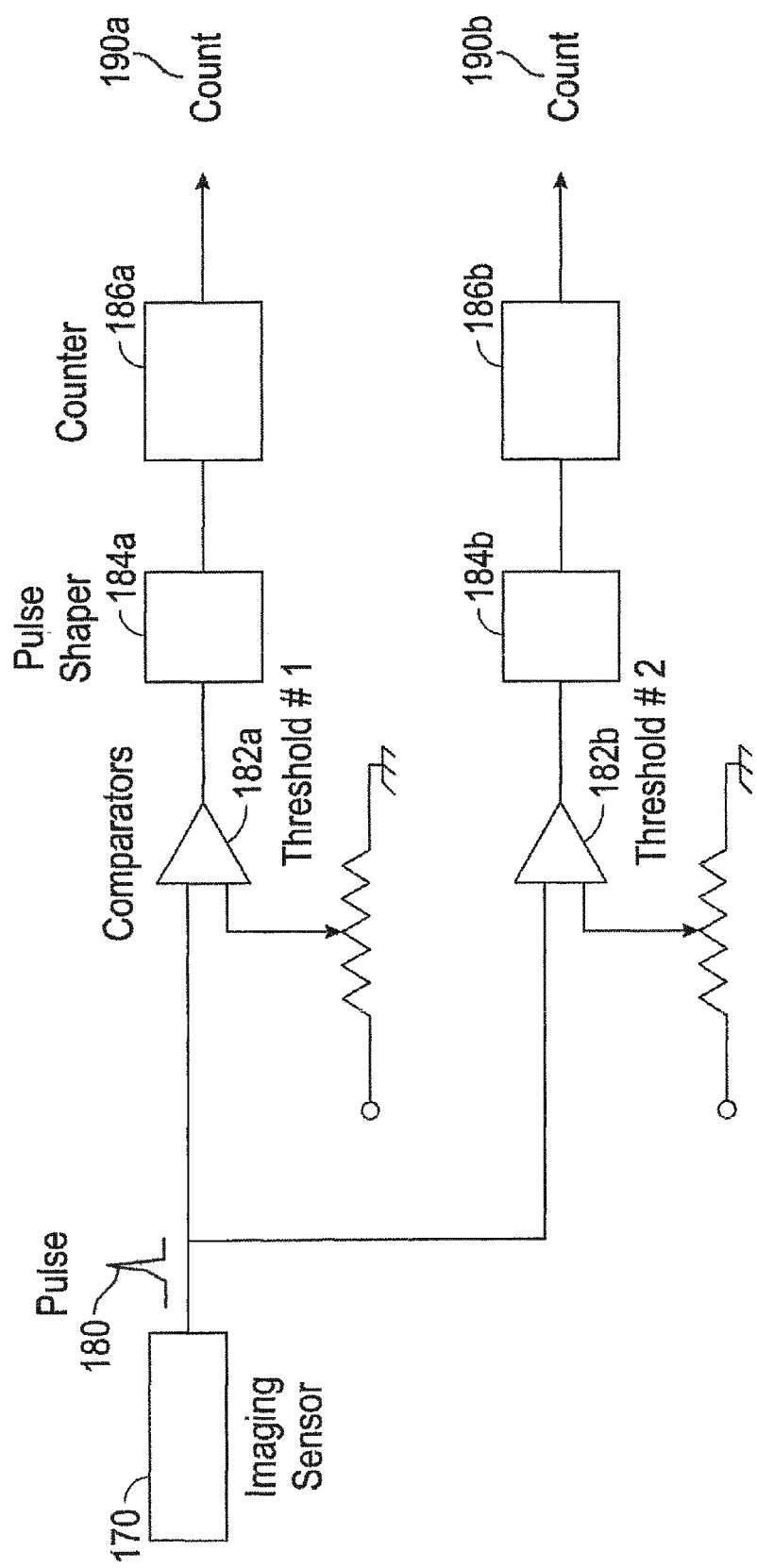
FIG. 2B is a schematic diagram that shows a photon-counting arrangement for measurement at two different energy levels.

The capability to count photons at different energy thresholds, as described with reference to FIG. 2B, allows the intraoral detector to differentiate between energy levels obtained from irradiating the subject and provides added dimension to the image data that is provided as a result of each exposure. This capability, described as multi-spectral or "color" x-ray imaging, enables information to be obtained about the material composition of a subject pixel. As is well known, two materials A and B can have different coefficients of attenuation $\mu$ that vary with the level of radiation energy, exposure E. At a given exposure, material A attenuates a photon with an energy that corresponds to material A. Similarly, radiation impinging on material B attenuates a photon with an energy that corresponds to material B. Where photons of these different energy values can be differentiated from each other, it is possible to identify one or both materials in the same pixel or voxel image element of the obtained image. This same basic behavior in response to radiation also allows some measure of capability to differentiate tissue types. Different linear absorption characteristics allow differentiation between various types of tissue, such as between bone types.

Color x-ray using photon counting detectors provides for low cost and low dose color x-ray imaging. The use of multi-spectral or "color" x-ray imaging can have a number of potential benefits of value for intraoral imaging. These include minimization of metal artifacts, separate reconstruction of soft and hard tissue, more efficient segmentation algorithms for tooth and bone features, improved pathology detection for cancer and other disease, and detection of trace materials or contrast agents.

According to an exemplary embodiment according to the application, chairside intraoral imaging apparatus 100 can have two or more interchangeable detectors 20, suitable for different imaging functions. For example, a conventional integrating image detector can be connected to processor 26 for radiographic imaging; a photon counting detector can be connected only when needed for tomosynthesis or radioscopic imaging. Keyed connectors or other mechanical or signaling mechanism can be used to indicate which type of detector is connected.

Among techniques that can be used for providing adjustable resolution and increasing acquisition speed are detector binning, described in more detail herein. Binning groups together uniform sets of adjacent sensor elements to provide a single, averaged value for the individual area of each set of pixels.

Source/Detector Alignment

Detector alignment can be difficult for dental or intraoral radiography. The detector position is within the patient's mouth and is not visible to the technician. Instead, the technician typically places the detector into some type of holder, and then inserts the holder into place in the mouth. The holder may have a bite plate or other type of supporting member that helps to position the detector appropriately. As is well known, holders of this type can be cumbersome and uncomfortable to the patient. Holders and other positioning devices are not error-proof, and positioning errors with these devices can mean that the images obtained are not suitable for diagnosis. Poorly aligned detectors can be the cause of problems such as cone cuts, missed apices, and elongation and related angulation or parallax errors, for example. These alignment problems can result in the need for re-takes, additional image captures to acquire an acceptable image. Re-takes are undesirable due to the additional x-ray radiation exposure to the patient and prolonged patient discomfort with the detector or sensor in the mouth.

Conventional x-ray sources have included aim indicators that help the technician adjust the position and angle of the x-ray source. Often these aim indicators use visible light to trace an outline that helps to center the radiation beam. These work well where the radiation detector can be seen, but fall short of what is needed where the detector is not visible, such as with intraoral imaging. The technician must guess or estimate both the position of the intraoral sensor and the angle of incidence of x-rays on the sensor.

Figures 3A, 3B:
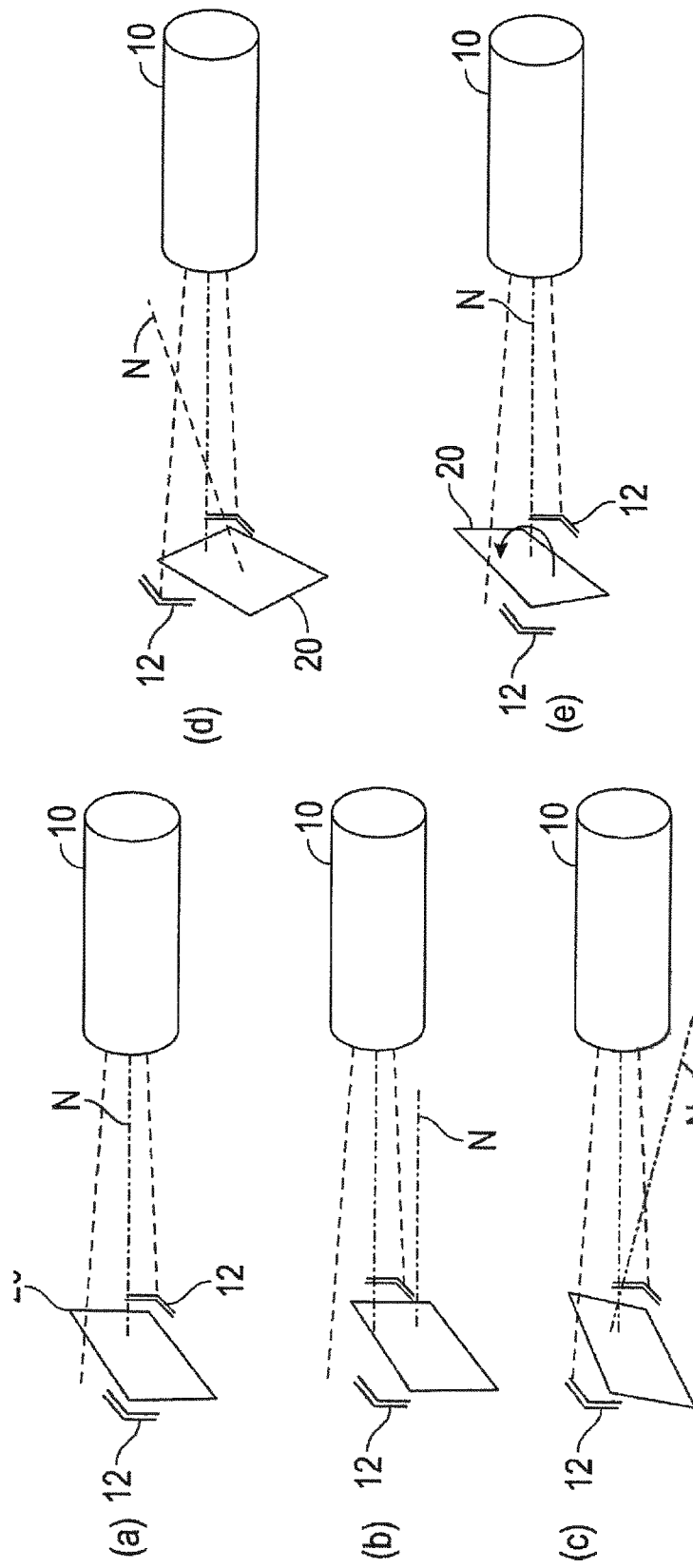
FIGS. 3A and 3B are simplified schematic block diagrams that show different aspects of the alignment problem.

The simplified schematic of FIGS. 3A and 3B show how mis-alignment between an x-ray source 10 and a detector 20 can occur. In these examples, x-ray source 10 provides visible light aim indices 12 used for aim centering. When correct aim alignment is achieved, shown at example (a), detector 20 is centered, as shown within aim indices 12. Aim is incorrect at examples (b) and (d).

For best imaging results, proper alignment with respect to angle, or angulation, is also needed. Incident radiation from x-ray source 10 is preferably orthogonal to detector 20 as shown in example (a). Line N in FIG. 3A, 3B indicates a normal, or orthogonal line, to the surface of detector 20. Examples (c) and (d) show incorrect angular alignment. In example (c), aim or centering is correct but angulation or pitch is incorrect. In example (d), both aim (centering) and angulation (pitch) are incorrect. In example (e), detector 20 is rotated in plane (roll).

It is instructive to note that the schematic examples of FIGS. 3A and 3B assume an orthogonal positioning of x-ray source 10 to detector 20. In some embodiments, an oblique orientation may be used.

Alignment and positioning are particularly important for volume imaging applications in which images taken at different angles are to be combined in some way to form volume image data.

In tomosynthesis, the relative movement between source and detector introduce further complexity into the alignment problem. It is generally most favorable for reconstruction processing to have the line or arc of movement disposed such that the spatial position of the source is within the same plane relative to the detector surface, or equidistant from the surface, so that movement aligns with pixel positions on the detector surface for each acquired projection image.

In order to better understand the parts and operation of the apparatus of the present invention, it is helpful to show how proper alignment can be detected by an imaging system. Referring to the schematic block diagram of FIG. 4, there is shown an intraoral imaging apparatus 22 that detects alignment of imaging detector 20 with x-ray source 10.

Figure 4:
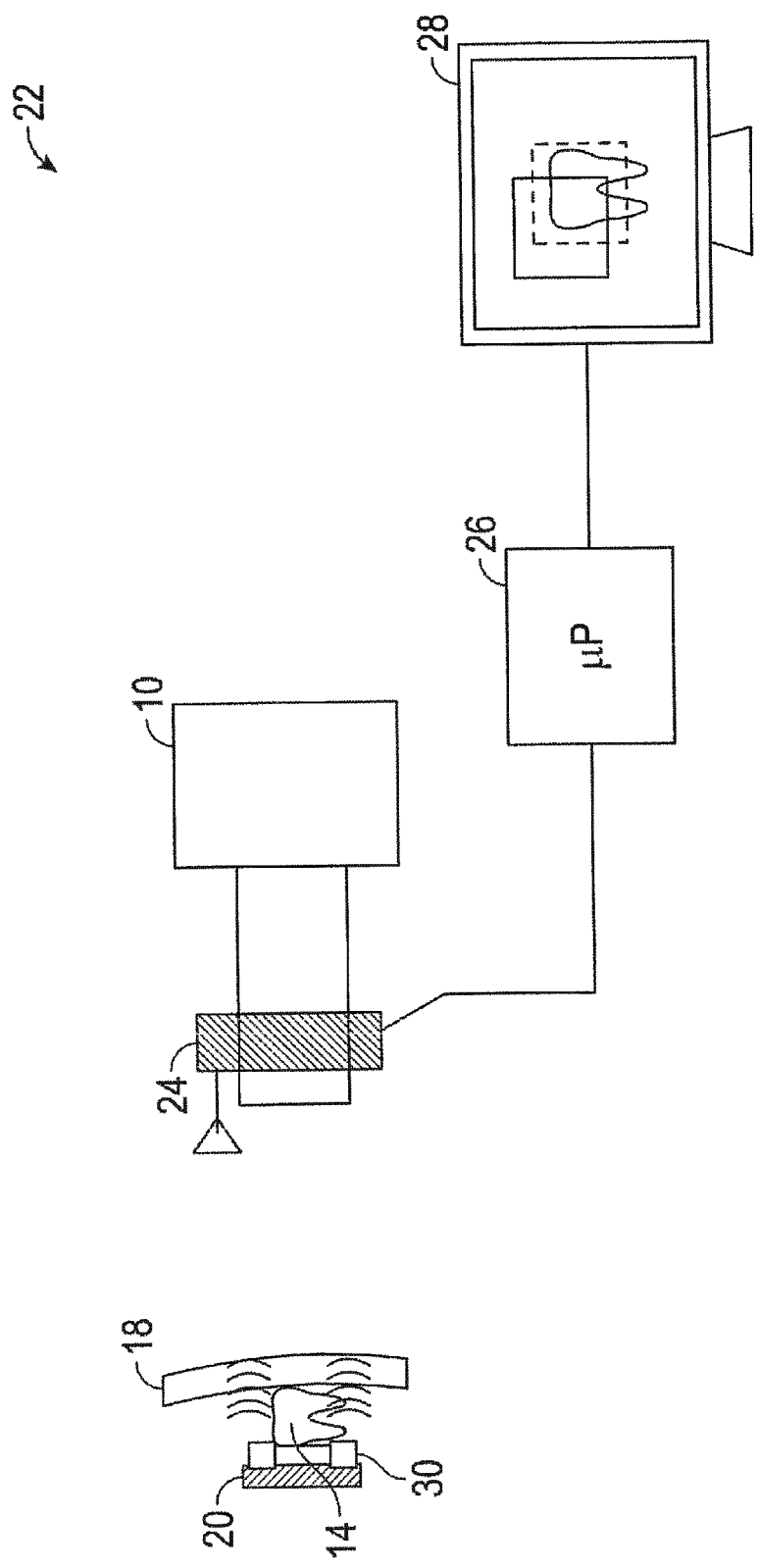
FIG. 4 is a schematic block diagram showing an imaging apparatus that calculates the lateral position and angular orientation of an intraoral image detector.

In the FIG. 4 arrangement, detector 20 is placed at a detector position that is adjacent to a tooth 14, inside a cheek 18 of the patient. Incorporated as part of detector 20 are a number of detectable elements 30, which are shown as electromagnetic signal emitters, such as radio-frequency (RF) emitters. Detectable elements 30 are typically spaced apart from each other in order to provide triangulation information. A sensor 24, itself aligned and positionally coupled with x-ray source 10, senses the presence of detectable element 30 in some way, such as by sensing emitted RF signals. Methods for energizing and sensing RF emitters, such as the tiny emitters used in RFID tags, for example, are well known to those in the signal detection arts. A control logic processor 26, in signal communication with one or more sensors 24, employs conventional trigonometric calculations based on the received signals from, or other detectable features of, detectable elements 30 and the known position of sensor 24 with relation to x-ray source 10. This is performed in order to determine the corresponding positional and angular alignment of detector 20 in the patient's mouth relative to x-ray source 10. An operator console display 28, a computer display monitor, then indicates alignment information for the operator and may recommend the needed adjustment settings. Sensors 24 are energizable to receive electromagnetic signals of one or more predetermined frequencies.

Figure 5:
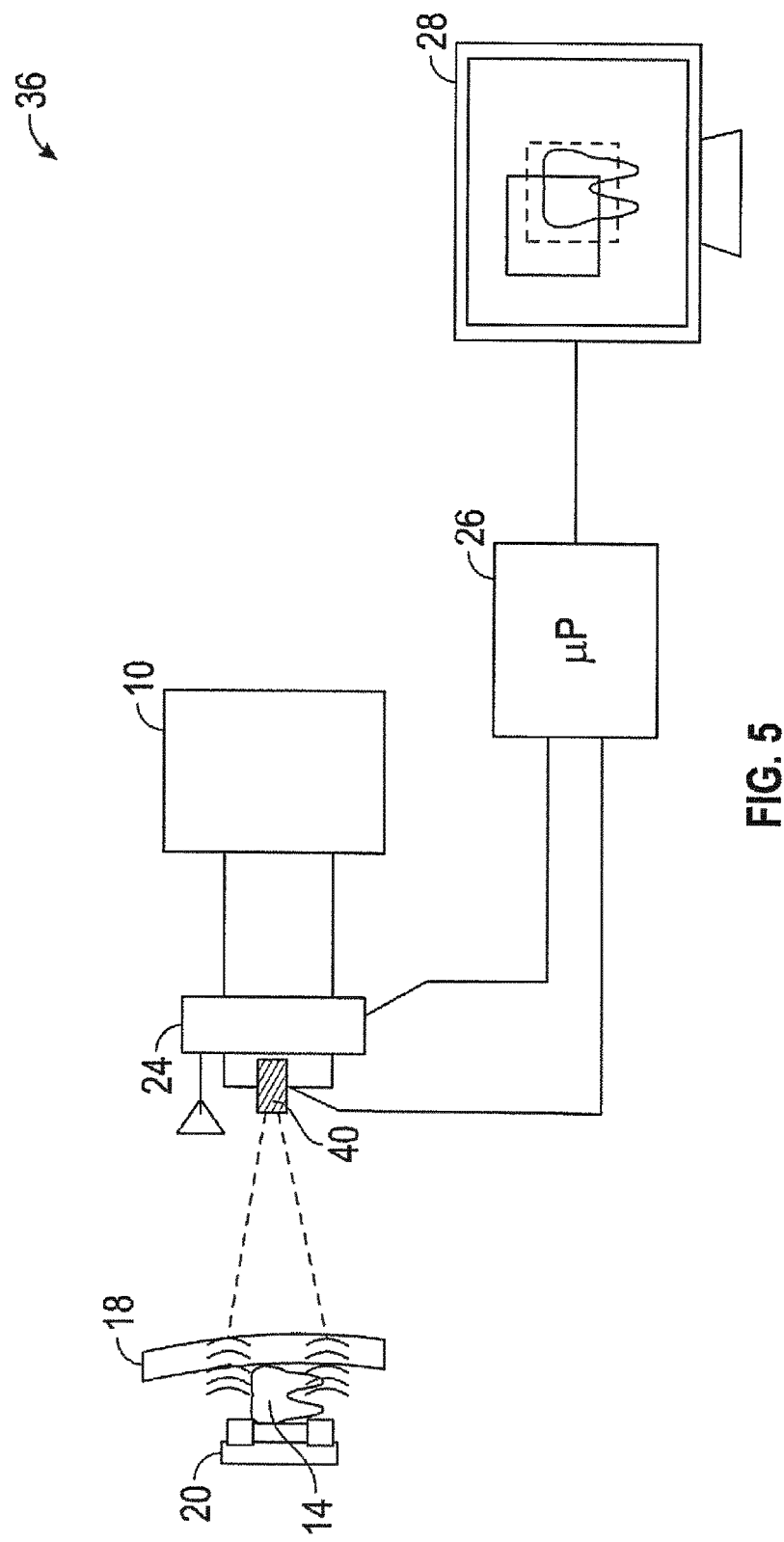
FIG. 5 is a schematic block diagram showing an imaging apparatus that calculates the lateral position and angular orientation of an intraoral image detector and projects a display onto the patient's cheek.

Certain exemplary method and/or apparatus embodiments of the present invention improve upon the basic system of FIG. 4 by providing alignment information to the technician where it can be more easily used, particularly where this information is needed in order to obtain the individual images used for forming a volume image. Exemplary alignment apparatus of the present invention can project an image onto the cheek or other portion of the dental patient as a guide for proper alignment of the x-ray tube with respect to the position and angle of the detector. Referring to an embodiment of an imaging apparatus 36 in FIG. 5, control logic processor 26 obtains alignment information in similar manner to that described in FIG. 4. In addition, as shown in FIG. 5, control logic processor 26 can also be in image data signal communication with a projector 40 for projecting an image onto the patient's cheek 18, lips, or face.

Figure 6A:
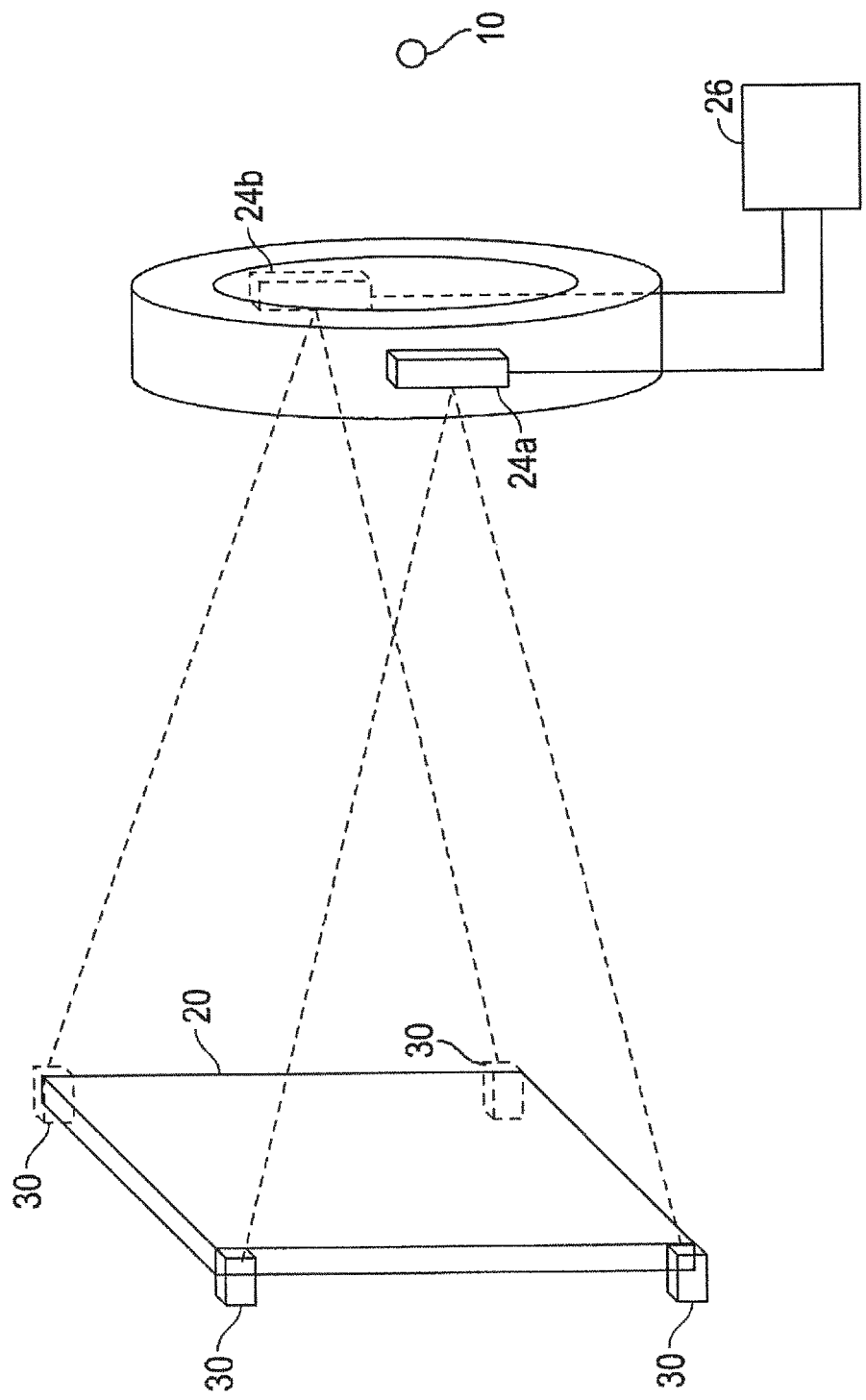
FIG. 6A is a schematic diagram that shows how triangulation is used for position detection in one embodiment of the present invention.

The perspective view of FIG. 6A shows, in schematic form, how triangulation can be used to indicate position and angle of detector 20 in order to determine alignment offset in one embodiment. Sensors 24a and 24b, RF transceivers in one embodiment, are at a known position relative to the x-ray source 10, such as mounted near the x-ray source on the x-ray tube, for example. Signal emitters or other type of detectable elements 30 are typically disposed in pairs, positioned at corners of detector 20. Each detectable element 30 has a detectable feature that can be sensed by sensors 24a and 24b. In one embodiment, each detectable element 30 is an RF device that generates an electromagnetic field, such as in response to a transmitted signal from its corresponding signal receiver, sensors 24a or 24b. Phase, intensity, or other characteristic of the emitted electromagnetic field is measured at the corresponding sensors 24a and 24b, and is used in order to determine relative distance between emitting and receiving components. For the RF detection embodiment of FIG. 6A, for example, when signals for each pair of emitters, acting as detectable elements 30, are in phase, good alignment has been achieved. An out-of-phase condition indicates poor alignment and can indicate the needed direction for adjustment. Sensors 24a and 24b are in signal communication with control logic processor 26.

In a similar manner, relative signal strength could alternately be used to indicate the position and angle of detector 20 with respect to the x-ray source for determining alignment offset. Using this approach in an RF embodiment, the nearest signal emitter acting as detectable element 30 has, correspondingly, the strongest intensity signal at sensor 24a or 24b. When the arrangement of FIG. 6A is used, signals of equal intensity emitted from all four emitters or other type of detectable element 30 indicate good alignment. When signal intensities vary, the pattern for their variation can be used to indicate which adjustments are needed. As one example, U.S. Patent Application Number 2009/0060145, entitled "Positioning Adjustment of a Mobile Radiology Facility" by Tranchant et al., describes a position detection system that uses triangulation and sensing of multiple emitted signals to compute alignment positioning. It can be appreciated that any of a number of different configurations can be used for determining proper alignment using one or more sensors 24 and detectable elements 30, as is well known to those skilled in the signal processing and position sensing arts.

Figure 6B:
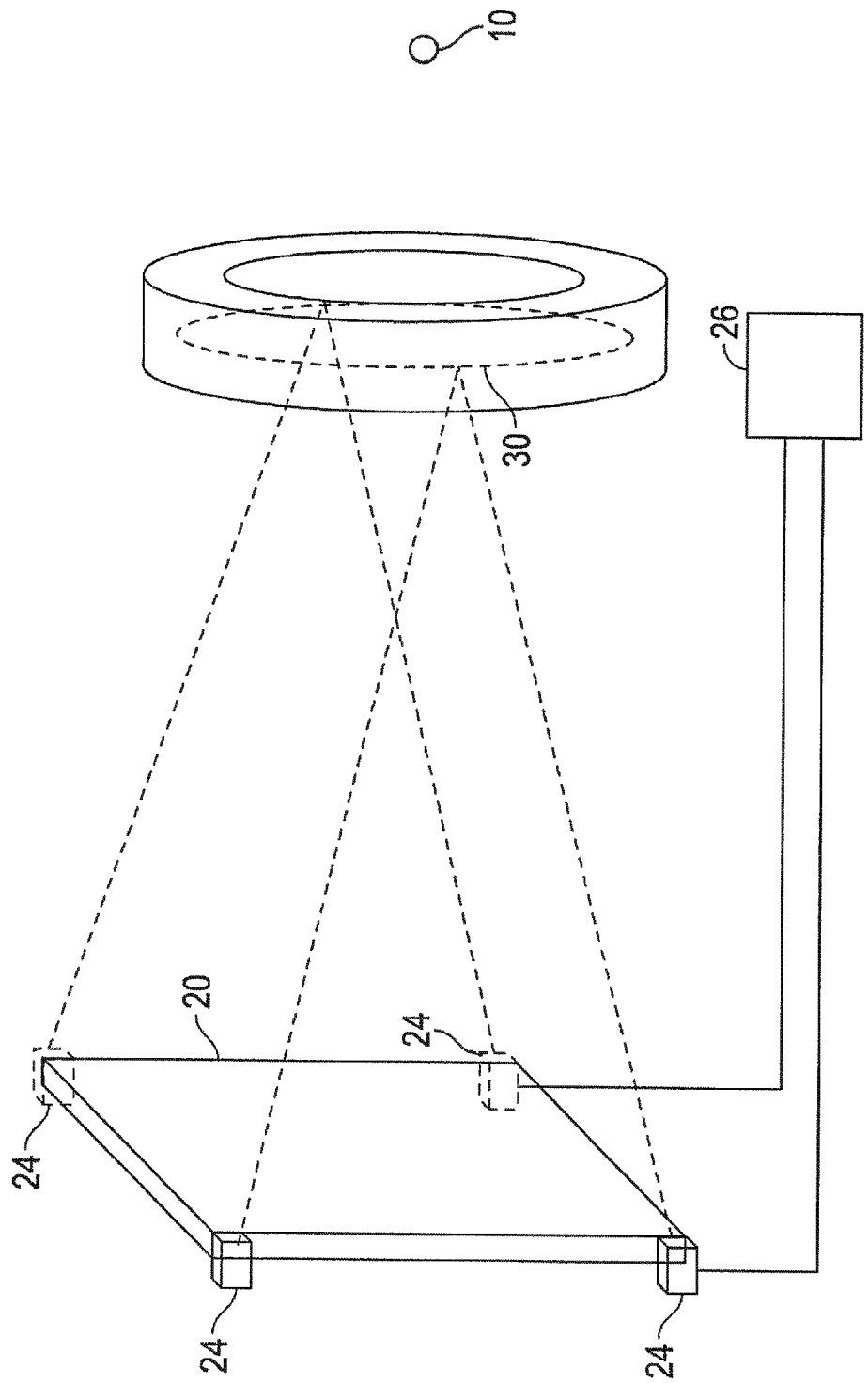
FIG. 6B is a schematic diagram that shows position detection in an alternate embodiment of the present invention.

In one alternative embodiment, shown in FIG. 6B, the emitter-detector arrangement that was shown in FIG. 6A is reversed, so that one or more emitters that provide one or more detectable elements 30 are mechanically coupled to x-ray source 10 and two or more sensors 24 are attached to detector 20. In the embodiment shown in FIG. 6B, for example, detectable element 30, shown in dashed outline, is a coil that generates an electromagnetic field that is sensed by sensors 24. Sensors 24 are in signal communication with control logic processor 26, either through a direct (e.g., wired) or an indirect (e.g., wireless) connection.

Alternate Alignment Mechanisms

In one exemplary embodiment, an intraoral scanner or other reflectance imaging sensor can be used as an aid to source alignment with the detector. The optical scan data obtained from a contour image or conventional reflectance image can be analyzed as a type of "scout" scan in order to determine the desired trajectory for the tomosynthesis scan.

In another exemplary embodiment, ultrasound imaging can also be used as an alignment aid for source positioning. Ultrasound can be particularly useful with its capability to image soft tissue structures within the anatomy.

It should be noted that CNT source alignment can be adjustable to control the trajectory of relative positional change of the radiation source for each subsequent image.

Figure 6D:
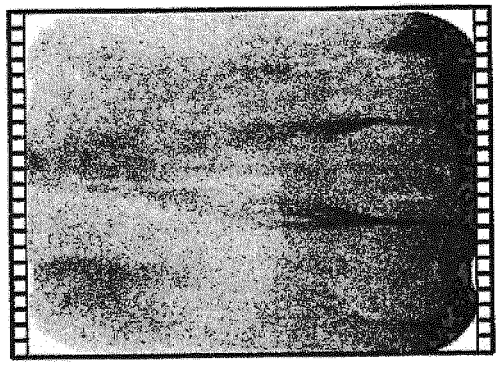
FIGS. 6D and 6E show how markers appear in the acquired image, along the borders of the imaged intraoral features.
Figure 6E:
Figure 6C:
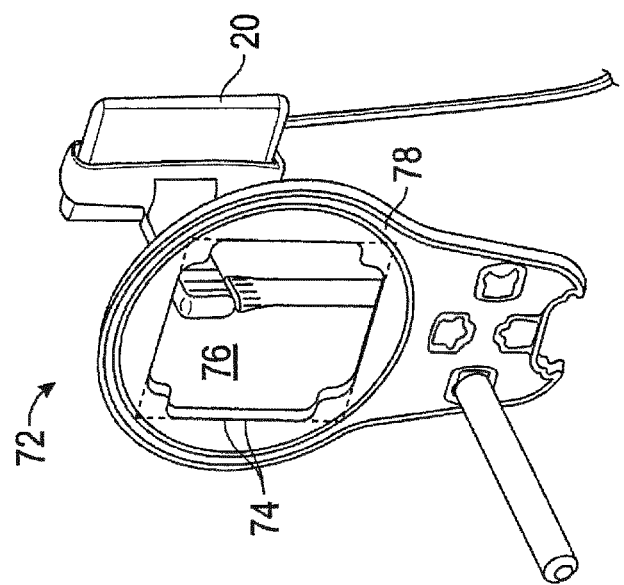
FIG. 6C shows a holder having an arrangement of radio-opaque alignment markers about a central opening.

One exemplary method and/or apparatus embodiment according to the application provides autofocus and alignment functions using an arrangement of embedded markers within a holder that is used for positioning the intraoral sensor. FIG. 6C shows a holder 72 for a frame 78 having an arrangement of radio-opaque markers 74 about a central opening 76 that orients the x-ray source 10 (not shown in FIG. 6C). FIGS. 6D and 6E show how the markers 74 appear in the acquired image, along the borders of the imaged intraoral features. Using the alignment markers allows image processing to correlate the positions of successively acquired images and to accurately register the projection images to each other for subsequent reconstruction.

It can be observed that solutions such as those shown in FIGS. 6A-6C can be used for alignment in any number of source-to-detector arrangements, as is described in more detail herein.

Projection of Outline Onto Patient or Other Alignment Feedback

Figure 7A:
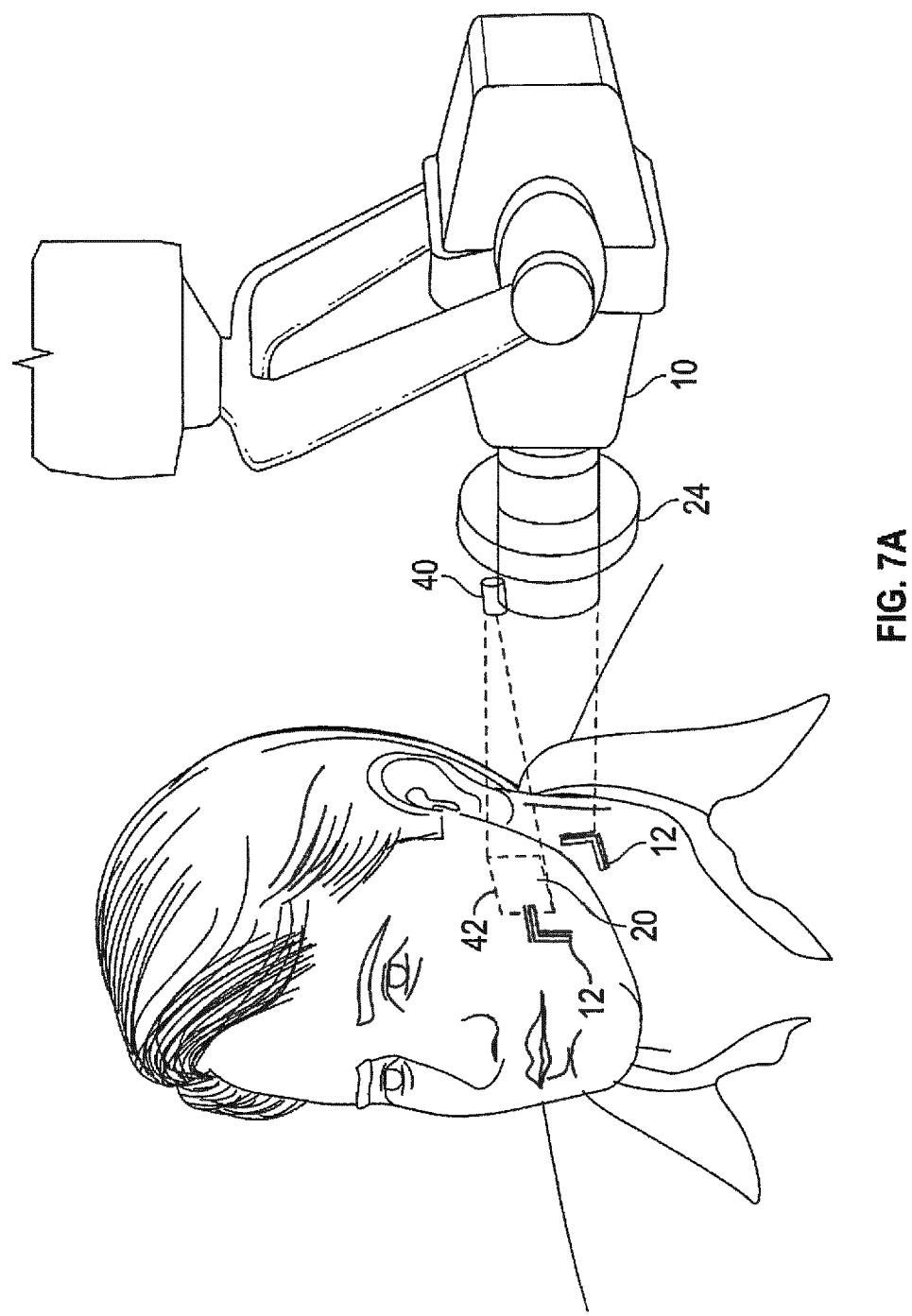
FIG. 7A is a perspective view showing an intraoral x-ray imaging apparatus according to one embodiment, in which alignment is not correct.
Figure 7B:
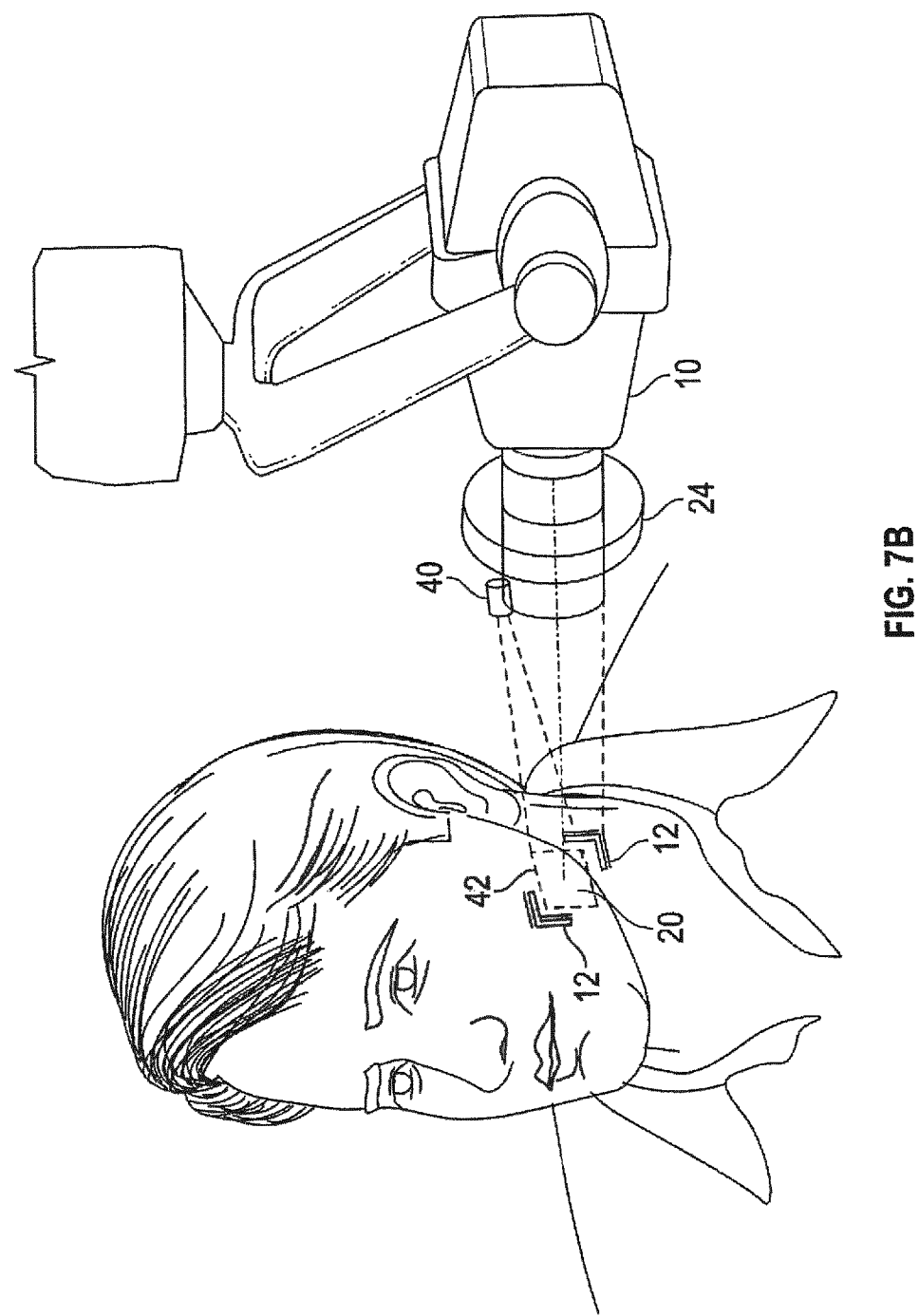
FIG. 7B is a perspective view showing an intraoral x-ray imaging apparatus according to one embodiment, in which alignment is correct.

Referring to the perspective views of FIGS. 7A and 7B, the added advantage of exemplary embodiments of the present invention that provide optional image projection is shown. Projector 40, positionally coupled to x-ray source 10, such as mounted in position toward the end of the x-ray tube or on some other portion of the x-ray system, for example, projects a two-dimensional image onto the patient's cheek in order to indicate a position 42 of the concealed detector 20 (shown in dotted outline) and, unless already provided by the x-ray source 10, also to indicate the aim indices 12 of the x-ray source. FIG. 7A shows an example in which aim alignment is incorrect, since position 42 is not aligned with aim indices 12. FIG. 7B shows an example in which aim alignment is correct, with position 42 centered between aim indices 12.

Projector 40 can be any of a number of types of imaging projector that can be mounted onto x-ray source 10. In one embodiment, projector 40 is a pico-projector, such as a Pico Projector Display from Microvision Inc., Redmond, WA, USA, for example. Devices such as these are advantaged for a number of reasons, including small size, low weight, and low power requirements. These pico-projectors, used in cell-phone and other highly portable electronic devices, scan one or more low-power lasers onto a display surface. The pico-projector requires a minimum of optical components for projection over a range of distances. The laser itself is turned on and off rapidly as needed, so that power is consumed only for those image pixels that are projected. This allows the pico-projector to operate at low power levels, so that battery power could be used for projector 40. Alternate embodiments use other types of electronic imaging projectors, such as those that employ a digital micromirror array such as the Digital Light Processor (DLP) from Texas Instruments, Inc.; an array of micro-electromechanical grating light valves, such as the Grating Light Valve (GLV) device from Silicon Light Machines, Inc.; or a liquid crystal device (LCD) including a Liquid Crystal on Silicon (LCOS) device.

Where lasers are used as illumination sources in projector 40, additional measures can be taken to minimize incidence of coherent laser light to the eyes of the patient or practitioner. Very low power lasers can be used, such as solid-state lasers, at scanning rates that deliver only a very small amount of light intensity at any point. A diffusive element may be provided in the light path, for example, to provide some scattering of the laser light, reducing intensity with little or no effect on the quality or utility of the projected image. Light-emitting diodes (LEDs) or other low-power solid-state illumination sources could alternately be used, such as organic LED (OLED) devices.

The image that is projected by projector 40 (FIGS. 7A and 7B) can have image content that is any of a number of forms and may include both aim indicia 12 for the x-ray source and position 42 indicator for detector 20. Alternately, where aim indicia 12 are already provided by the x-ray system, projector 40 may only provide a projection showing position 42. Because projector 40 employs a two-dimensional imaging device, the displayed image can have multiple parts and may include additional text fields, direction markers, and other elements. Position 42 may be shown in outline form, as shown in FIGS. 7A and 7B, or may be represented in some other way. In one embodiment, the value of angular offset of detector 20 is indicated on the patient's cheek as a displayed numerical message. Alternately, animation or other capabilities of projector 40 could be used to provide, as image content, additional position and angle information.

Color can be used to help indicate the relative amount of alignment offset in various ways. For example, even with the outline of detector 20 projected on the cheek surface, it can be difficult for the technician to know how to adjust for angular alignment. Display of indicia 12 and position 42 in different colors can help to guide the technician in adjusting the angle of the x-ray tube until both aim indicia 12 and position 42 display in the same color, for example. Blinking of the display or of different portions of the displayed elements can also help to indicate and guide alignment adjustments. An audible beep may be provided to indicate acceptable or unacceptable alignment. Stationary indicators, such as arrows or target symbols can be projected as image content onto the cheek of the patient. Animation can be provided to guide adjustment.

In one embodiment, the projected image from projector 40 (FIG. 7B) instructs the technician on how to re-aim x-ray source 10 or how to adjust the position of the treatment chair in order to set up for the next image in the sequence. Projected color, patterning, alphanumeric text, animation, flashing or blinking, or other mechanism can be used to guide positioning adjustment between image captures.

A patient head support apparatus is provided in order to stabilize head position during the tomosynthesis image acquisition cycle. It should be noted that any type of headrest or other support mechanism cannot be metal or other highly radio-opaque material. The patient head support apparatus can be donut-shaped, expandable, or inflatable, for example.

Collimation

For select exemplary method and/or apparatus embodiments, collimation is needed in order to constrain the radiation field to the region of interest (ROI) within the patient's mouth.

One beneficial aspect of collimation relates to eliminating or reducing cone-cutting, in which excess radiation from the projected x-ray is incident on areas outside the region of interest.

A difficulty with distributed source arrangements such as CNT arrays relates to the need for appropriate collimation of the radiation. Among its functions, collimation controls the spread of radiation energy so that radiation is appropriately directed to the anatomy of interest and that the radiation field does not extend beyond the outer edges of the imaging receiver. Collimation also helps to reduce scatter. With CNT and other types of small x-ray sources in an array, collimation presents particular challenges. One set of problems relate to dimensional constraints. Because the spacing between x-ray sources is typically small, it can be difficult to effectively isolate the radiation energy from any individual source; crosstalk can occur, making it difficult to clearly define edges of the radiation field. Still other complexity relates to identifying the radiation field for imaging from each source. With conventional radiography sources, the problem is readily solved: a light source that is coupled to the radiography source can be used to outline or otherwise highlight the radiation field, using the collimator edges themselves to outline the extent of the radiation field. However, it can be impractical or impossible to provide the corresponding dual-use arrangement using collimator openings provided for CNT and other types of distributed array sources.

Figure 8B:
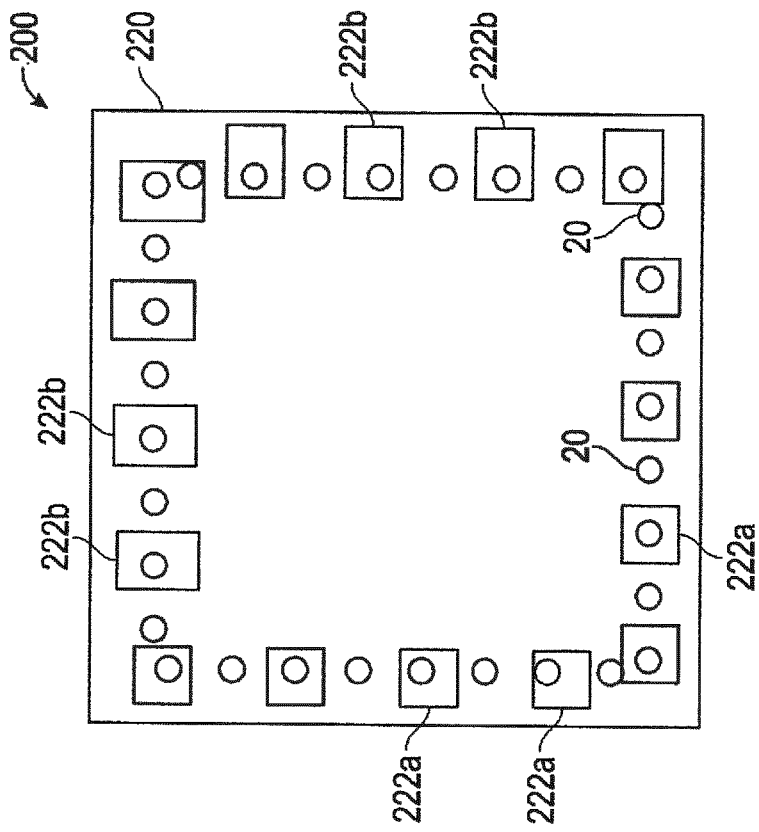
FIG. 8B is a bottom view showing a collimator plate assembly with apertures of different aspect ratios.
Figure 8A:
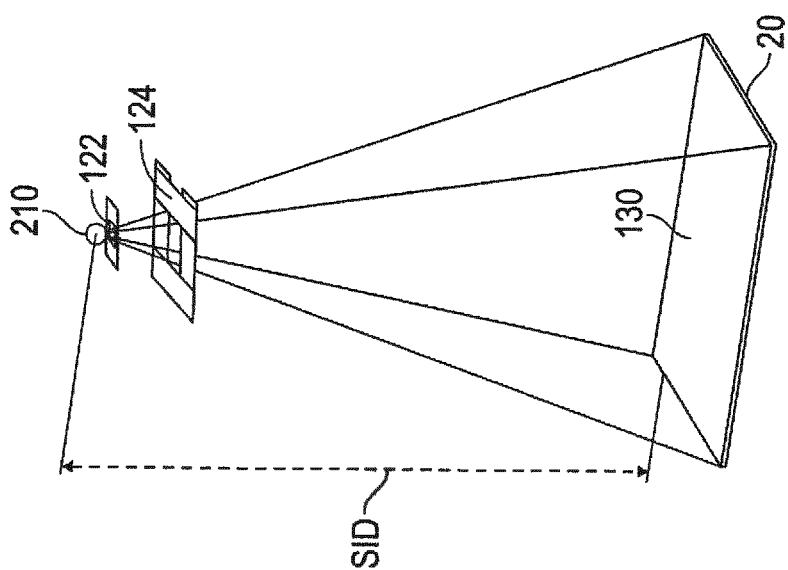
FIG. 8A is a bottom view that shows a radiation source assembly with collimation in a substantially square arrangement.

The simplified schematic view of FIG. 8A shows some of the geometric considerations and relationships that relate to x-ray collimation for a single x-ray source 210 in general and establish some definitions useful in subsequent description of collimation for an array of x-ray sources. X-ray source 210 is idealized as a point source, to a first approximation. Radiant energy from source 210 is directed along a radiation path that extends through a first aperture 122 that is typically very close to source 210 and may even be optional under some conditions for very small x-ray sources. The radiant energy then continues along the radiation path through a second aperture 124 that shapes an x-ray field 130 on a detector 20. The shape and dimensions of the radiation path that determine the aspect ratio of x-ray field 130 are then determined by the geometric constraints such as aperture 122, 124 size and location relative to the source 210 and to each other and source-to-image distance (SID). The shape of x-ray field 130 is typically bounded by the dimensions of detector 20 but may be smaller and of a different shape, depending on the anatomy being imaged. It must be noted that FIG. 8A shows geometric relationships for a single source 210; embodiments described subsequently have multiple x-ray sources 210, each having collimation along its radiation path in a similar manner to that shown in FIG. 8A.

According to an exemplary embodiment according to the application shown in FIG. 8B, array of sources 20 can be used with a rotatable collimator plate assembly 220 to form radiation fields of various shapes and aspect ratios depending on the dimensions of apertures 222a, 222b, rotation angle of collimator plate assembly 220, and the arrangement of corresponding sources 20 that are energized in the energization sequence. Thus, for example, with respect to FIG. 8B, a radiation source assembly 200 has a generally square shape with sources 20 distributed along the sides of the square. Collimator plate assembly 220 in FIG. 8B has apertures 222a and 222b of more than one aspect ratio. One set of apertures 222a is square; the other apertures 222b are rectangular. By rotating collimator plate assembly 220 to different positions and energizing the corresponding apertured sources 20 for the given radiation field shape, the sources 20 can be used in sequence to provide the needed radiation field shape and angular change for tomosynthesis.

Figure 8E:
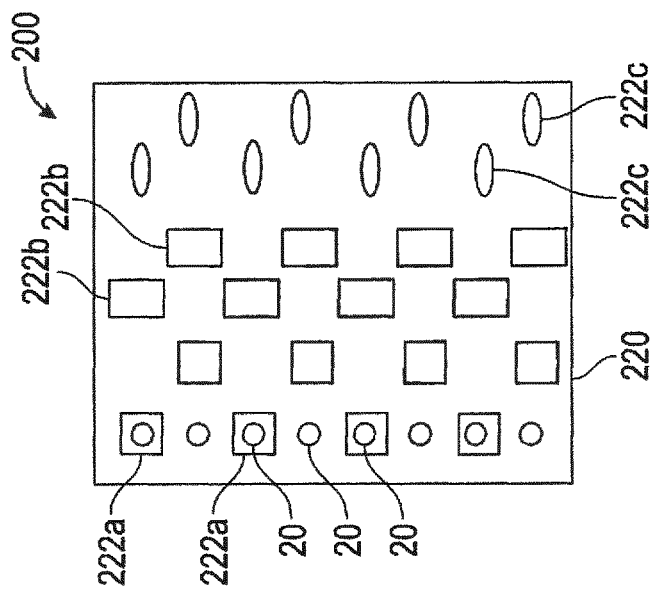
FIG. 8E is a bottom view that shows a collimator plate having paired sets of apertures of different aspect ratios.
Figure 8D:
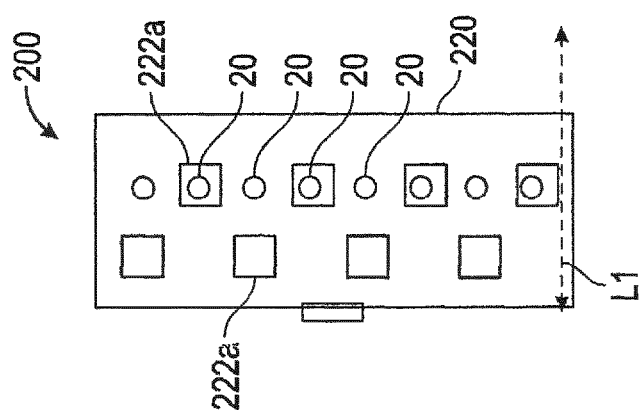
FIGS. 8C and 8D are bottom views that show an alternate collimator plate arrangement that is translated in a linear direction to position different sets of apertures over different subsets of the radiation source array.
Figure 8C:
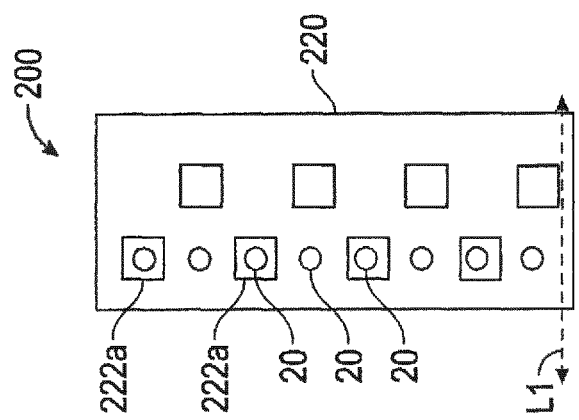

FIGS. 8C and 8D show another alternate arrangement in which collimator plate assembly 220 is translatable back and forth in a single direction, along the direction indicated by a line L1. In this example, radiation source assembly 200 is a linear array of sources 20. A set of square apertures 222a are arranged so that a subset of half of the apertures align to sources 20 with plate assembly 220 in a first position (FIG. 8C) and the subset with the other half of the apertures align to sources 20 with plate assembly 220 in a second position (FIG. 8D). FIG. 8E shows another arrangement, in which three different types of apertures are provided, a set of square apertures 222a in two subsets to be positioned in similar fashion to those shown in FIGS. 8C and 8D, a set of rectangular apertures 222b, and a set of oval apertures 222c, also used in a similar manner. Aperture 222 shapes can be inter-mixed (not shown).

Figure 8F:
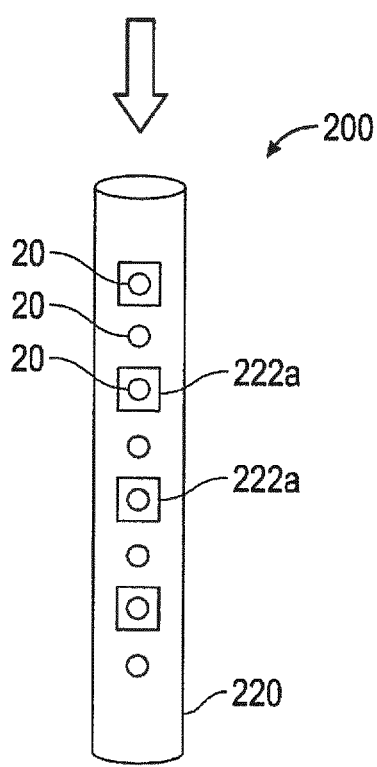
FIG. 8F is a view of a collimator that is curved and translated linearly along a linear distributed source array.
Figure 8G:
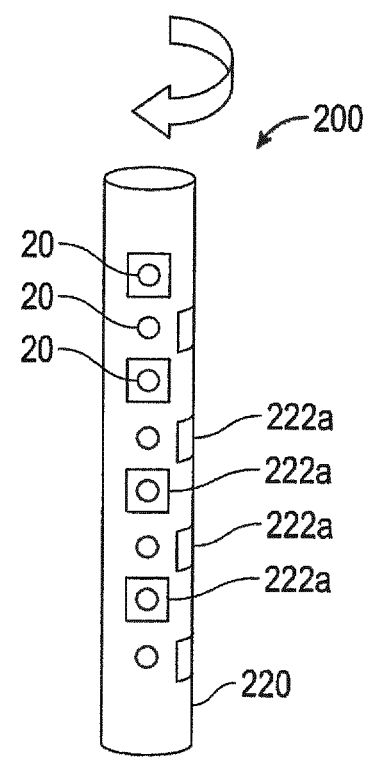
FIG. 8G is a view of a collimator that is curved and translated by rotating about a linear distributed source array.

FIGS. 8F and 8G show another alternate embodiment in which collimator plate assembly 220 has a generally curved or tubular shape, with apertures 222a arranged for x-ray sources 20 in a linear radiation source assembly 200. In the arrangement of FIG. 8F, collimator plate assembly 220 is moved in linear fashion to shift apertures 222a between subsets of x-ray sources 20. In the arrangement of FIG. 8G, collimator plate assembly 220 is rotated about the linear array to shift apertures 222a between subsets of x-ray sources 20.

Collimator plate assembly 220 can be formed from a pair of metal plates, spaced apart from each other to form apertures 122 and 124 (FIG. 8A) and with apertures 124 sized and positioned for suitable beam shaping. Apertures are aligned with source 20 positions based on the needed beam profile and angle. For collimation control, near-source apertures 122 can be in fixed positions, with only the far apertures 124 adjustable.

Scan Sequence for Tomosynthesis Imaging

The alignment apparatus that is provided by the triangulation sensing apparatus of FIG. 6A or 6B can be used to assist in capturing a series of images of the same tooth or other structure, taken in quick succession and each at a slightly different angle, for forming a limited-angle volume image. As noted in the background section given previously, this type of volume imaging can have diagnostic value and advantages over a single x-ray image, but without requiring the expense and dose requirements of full-fledged CBCT imaging. In addition, unlike with CBCT imaging, the limited-angle volume image can be acquired with the patient seated in the treatment chair.

Figure 9A:
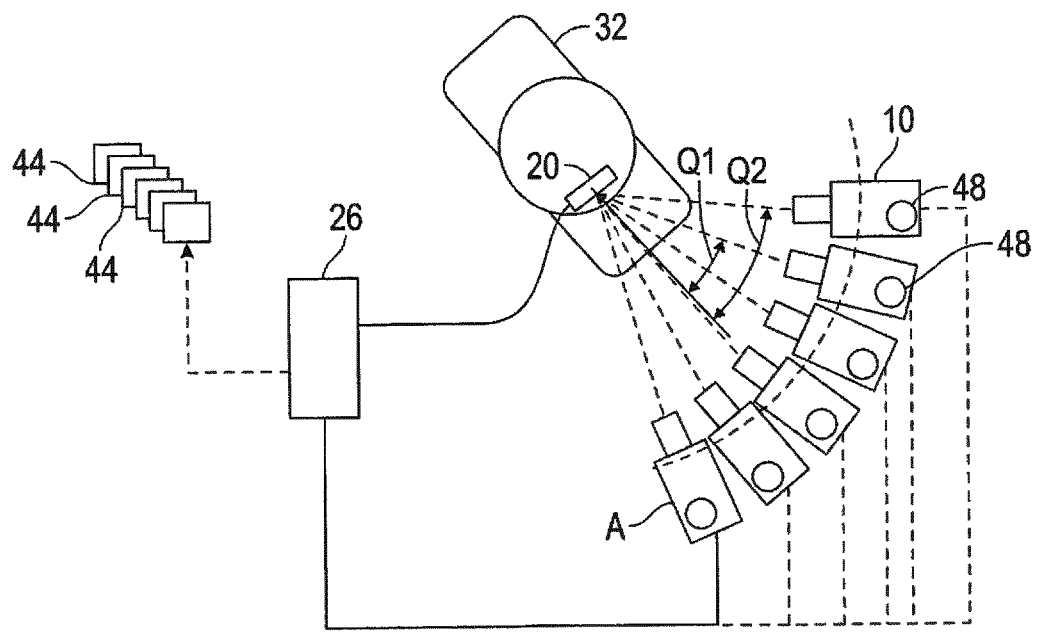
FIG. 9A is a schematic block diagram that shows an imaging pattern used for obtaining a volume image from a limited number of x-rays.

Referring to FIG. 9A, there is shown, from a top view, a schematic block diagram of an imaging pattern used for obtaining a limited-angle volume image from a patient 32 using a limited number of x-rays from a single source 10 and a digital detector. X-ray source 10 is used to direct exposure to detector 20 from a number of angular orientations, shown as capture or exposure angles in FIG. 9A, along a non-linear, curved or arcuate path A. At each of two or more exposure angle positions, with two called out by way of example as angles Q1 and Q2 in FIG. 9A, radiation energy is directed to detector 20 and the corresponding image data from the digital detector obtained by control logic processor 26 and stored as a component or projection image 44, indexed according to the relative acquisition geometry for the image, such as by the exposure angle orientation. In this way, one component image 44 is obtained and stored for each exposure angle. Control logic processor 26 can then generate a volume image as a composite image, using the combined data from the individual component projection images 44.

It should be noted that the pattern traced by changes in the relative position of the x-ray emitter to the detector, as shown in the top view of FIG. 9A for example, can be linear or curved.

Additional sensing components and logic associated therewith are used to provide positional and angular information about each image that is obtained. In one embodiment, for example, fixed positional and angular coordinates are assigned to an initial spatial position and angular orientation of x-ray source 10. Then, system logic records the changed position and angle that correspond to each imaging position in the series of images that are obtained. This data then provides the needed reference geometry for reconstruction of the 3-D volume image from a series of 2-D image captures. Spatial position data can be obtained in a number of ways, such as using an angular sensor 48 that is coupled with a gantry or other transport apparatus that is used for movement of x-ray source 10, for example.

Figure 9B:
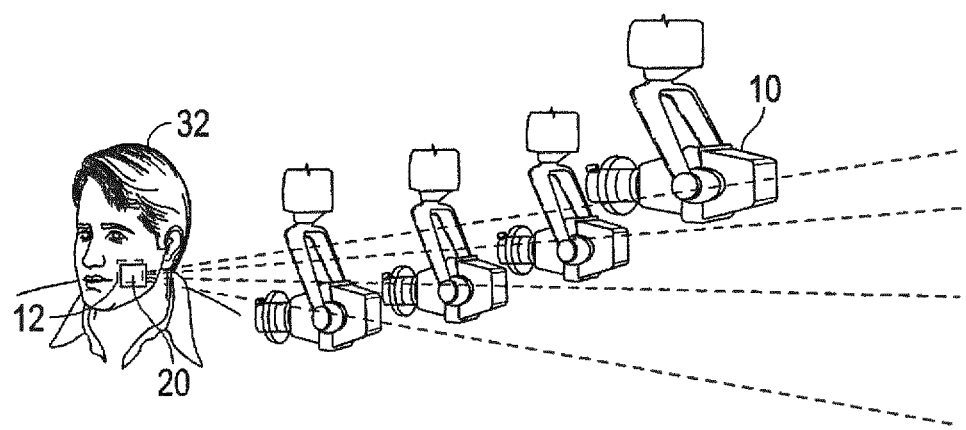
FIG. 9B is a perspective view showing how different positions of the x-ray emitter relative to the patient provide individual images for use in forming a volume image.

In order for this type of limited-angle volume imaging to work correctly, the angular orientation and spatial arrangement of x-ray source 10 relative to detector 20 must be known for each projection image acquired throughout the imaging cycle, so that the component data that is obtained can be properly aligned and correlated between projection images. For the embodiment shown in FIG. 9A and in the perspective view of FIG. 9B, the head of patient 32 and spatial position of detector 20 (shown in dashed outline in FIG. 9B) are rigidly fixed in position while x-ray source 10 is moved orbitally from one relative angular orientation to the next. It may be necessary to mechanically fix the spatial position of detector 20 relative to the subject that is being imaged. With respect to FIGS. 9A and 9B, for example, one or more bite blocks or a clip-on device may be useful for rigidly fixing detector 20 at a position within the mouth of patient 32.

Figure 10B:
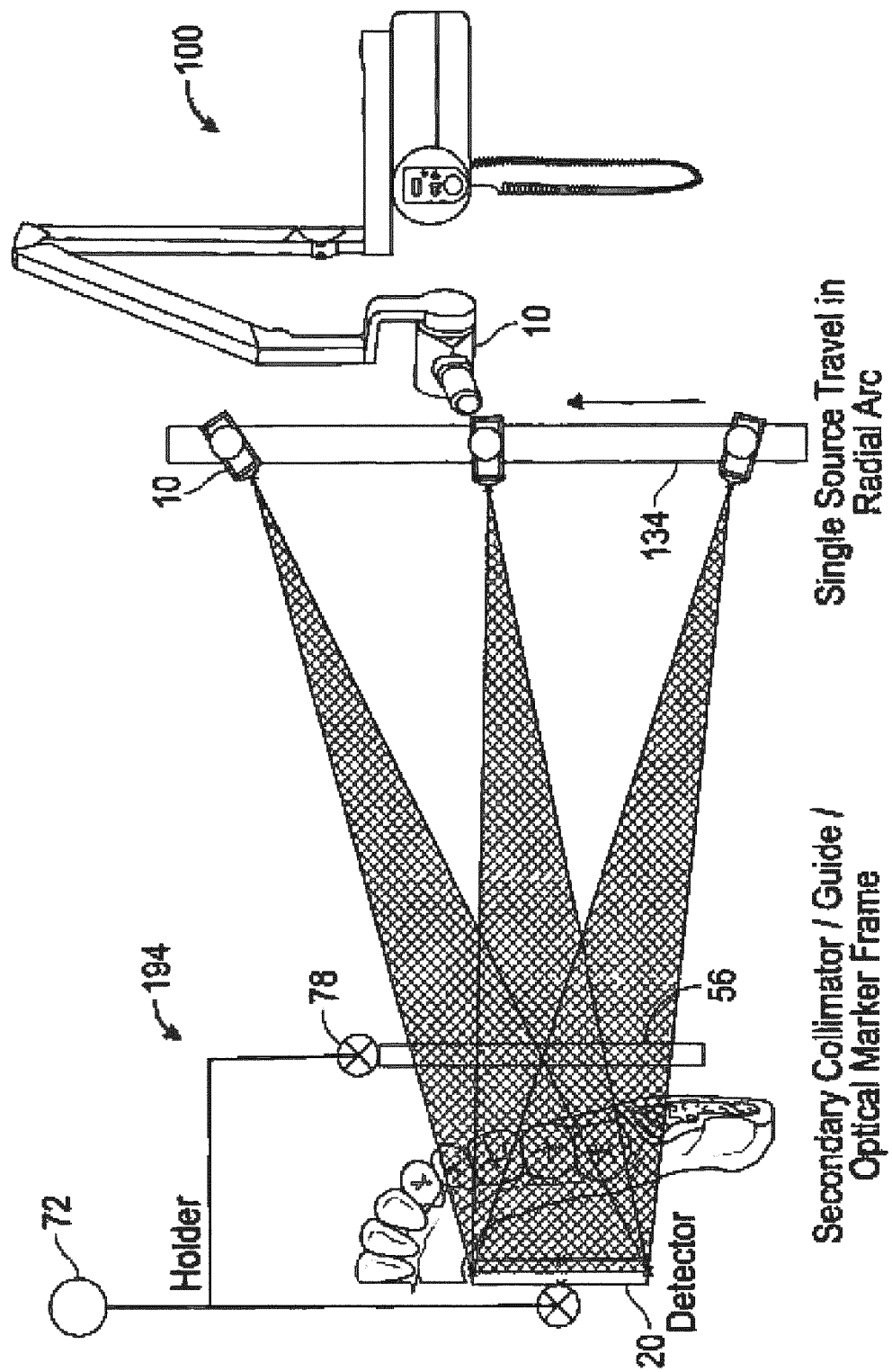
FIG. 10B is a schematic diagram that shows an intraoral imaging apparatus for tomosynthesis imaging with the x-ray source transported along a linear track.

FIG. 10A is a schematic diagram that shows an exemplary intraoral imaging apparatus for tomosynthesis imaging with x-ray source 10 transported along a curved or arcuate track 132. Arcuate track 132 is curved to approximate an arc that is substantially centered at the detector position. Detector 20 is held in the patient's mouth, mounted in holder 72. Holder 72 provides a type of positioning apparatus that correlates the detector position with respect to the collimator. Frame 78, suspended outside the mouth, provides an aim and alignment device for x-ray source 10 as well as a holder for positioning the secondary collimator 56. The schematic diagram of FIG. 10B shows a similar exemplary arrangement for apparatus 100 using a linear track 134. In the FIG. 10B embodiment, the x-ray source 10 pivots to different angles as it is translated along the linear path, thereby emulating the radial arc translation of FIG. 10A.

In the FIGS. 10A and 10B embodiments, detector 20 is rigidly coupled to frame 78, as was shown previously in the example of FIG. 6C. Holder 72, acting as a positioning apparatus 194 for correlating detector and collimator positioning, fixes the relative position of detector 20 and frame 78. For different patient head sizes, different size holders or different holder settings can be used. Alternate embodiments can use various arrangements of sensors and encoders to provide mechanical or sensed positioning apparatus for positioning of detector 20 relative to the collimator 56 and to frame 78, using signals obtained from one or more sensor and encoder devices.

Figure 10C:
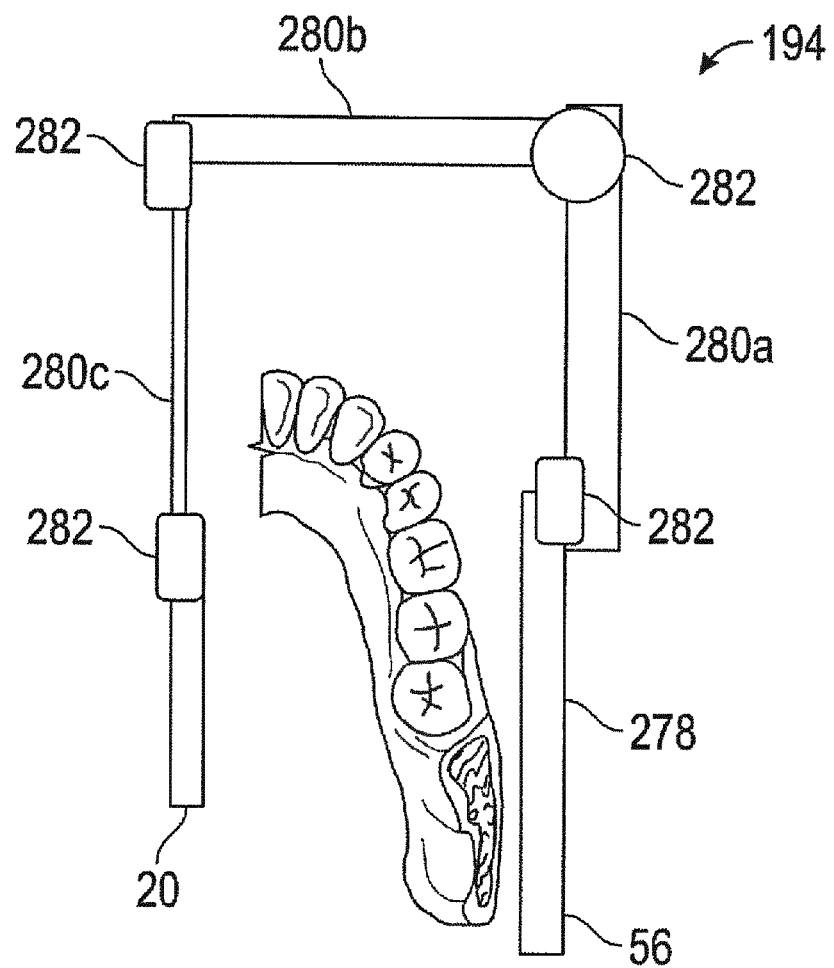
FIG. 10C is a top view schematic that shows a frame having multiple articulated sections at each adjustable joint for reporting sensed extension and rotation data.

The schematic top view of FIG. 10C shows an exemplary frame 278 embodiment having multiple articulated sections 280a, 280b, 280c with an encoder 282 at each adjustable joint for reporting sensed extension and rotation data. This arrangement provides a positioning apparatus 194 that allows resizing for the patient and provides repositioning of detector 20 relative to collimator 56, with sensed data available for correlating component positions relative to a reference position and relative to each other. Alternately, an accelerometer or electromagnetic, magnetic, or radio-frequency (RF) sensing may be provided and used as positioning apparatus 194 for correlating detector 20 position to the secondary collimator 56 and relating these positions to the position of the x-ray source at any acquisition angle in a tomosynthesis sequence.

Figure 11B:
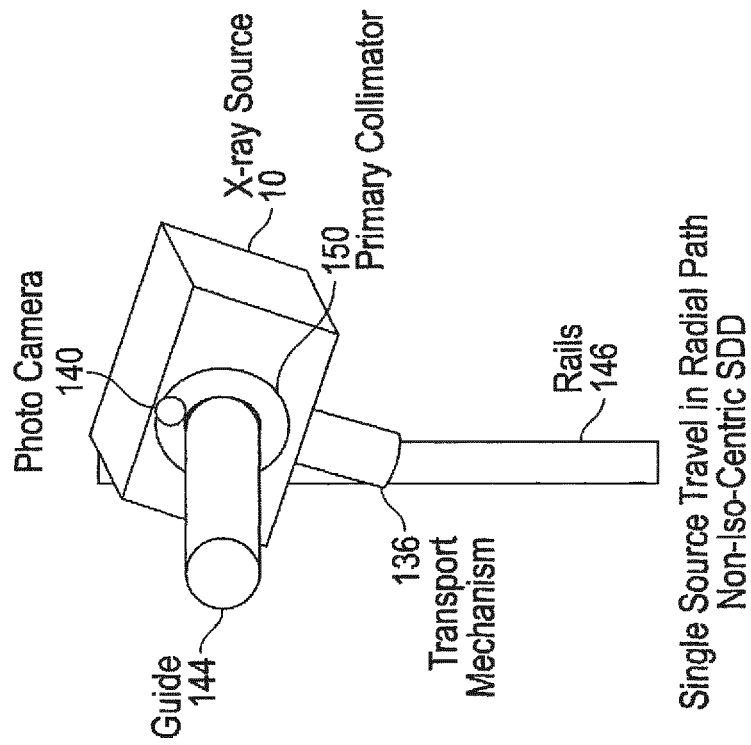
FIG. 11B is a perspective view that shows x-ray source configuration for the linear path arrangement shown in FIG. 10B.
Figure 11A:
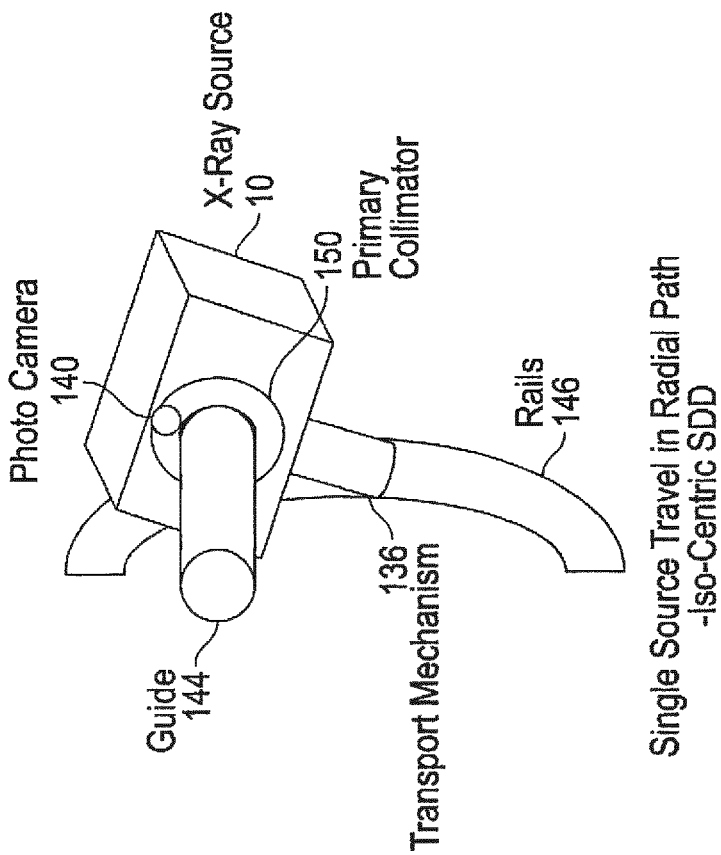
FIG. 11A is a perspective view that shows x-ray source configuration for the radial path arrangement shown in FIG. 10A.

FIG. 11A is a perspective view that shows a configuration of x-ray source 10 for the radial path arrangement shown in FIG. 10A that provides an exemplary iso-centric signal-to-detector distance (SDD). X-ray source 10 travels along rails 146 to follow curved or arcuate track 132 (FIG. 10A), driven by a transport 136. Source 10 has a primary collimator 150 that is integral to the source hardware. In the context of the present disclosure, the designation "primary collimator" applies to any collimator(s) integral to, and not separable from, the x-ray source. A secondary collimator is provided using frame 78, as described subsequently. A camera 140 that is coupled to guide 144 can be used to assist in source/detector alignment. The perspective view of FIG. 11B shows an alternate configuration for an exemplary linear transport, with a non-isocentric SDD.

Figure 12A:
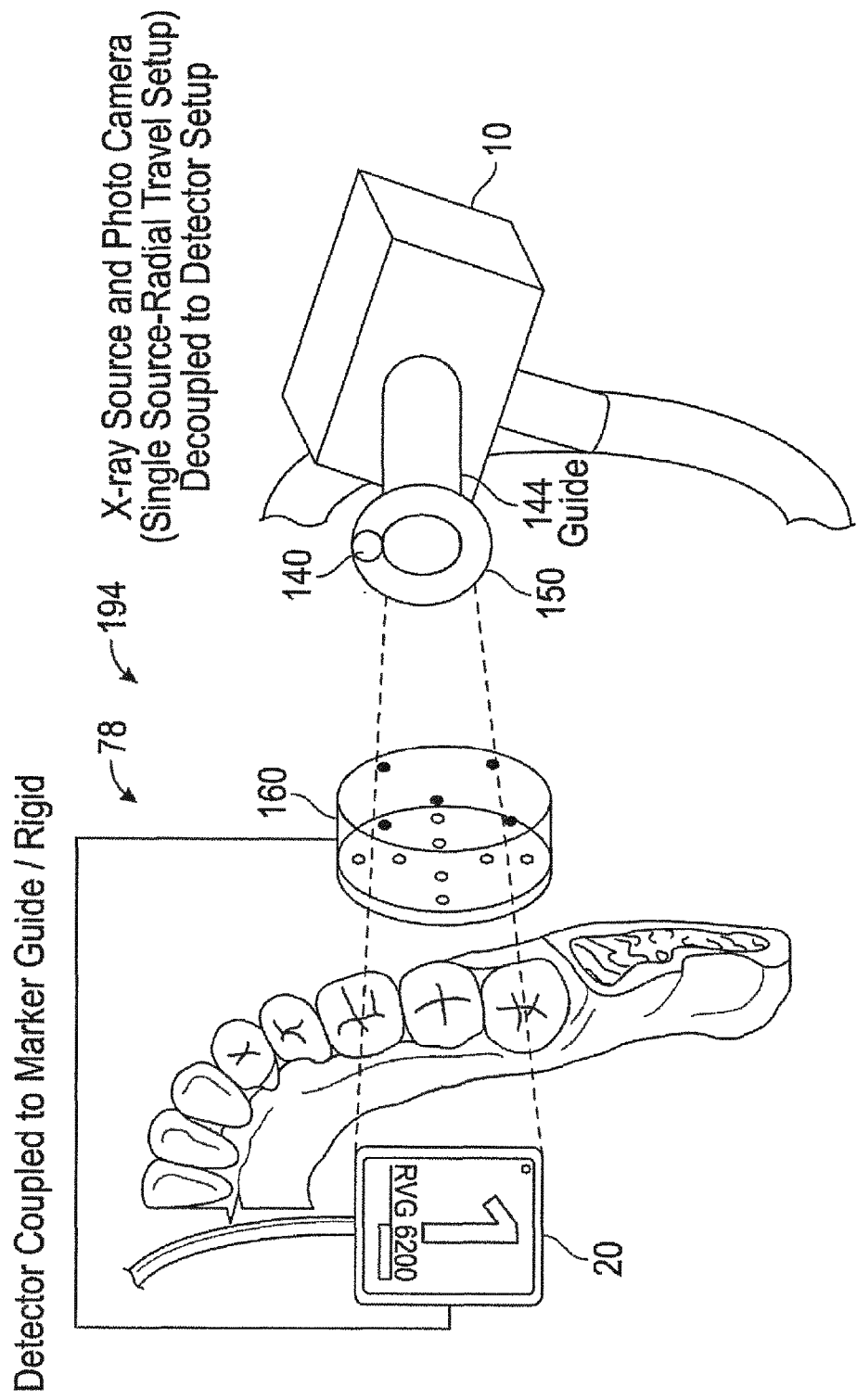
FIG. 12A is a schematic diagram that shows the use of a marker guide that is coupled with the intraoral detector.
Figure 12B:
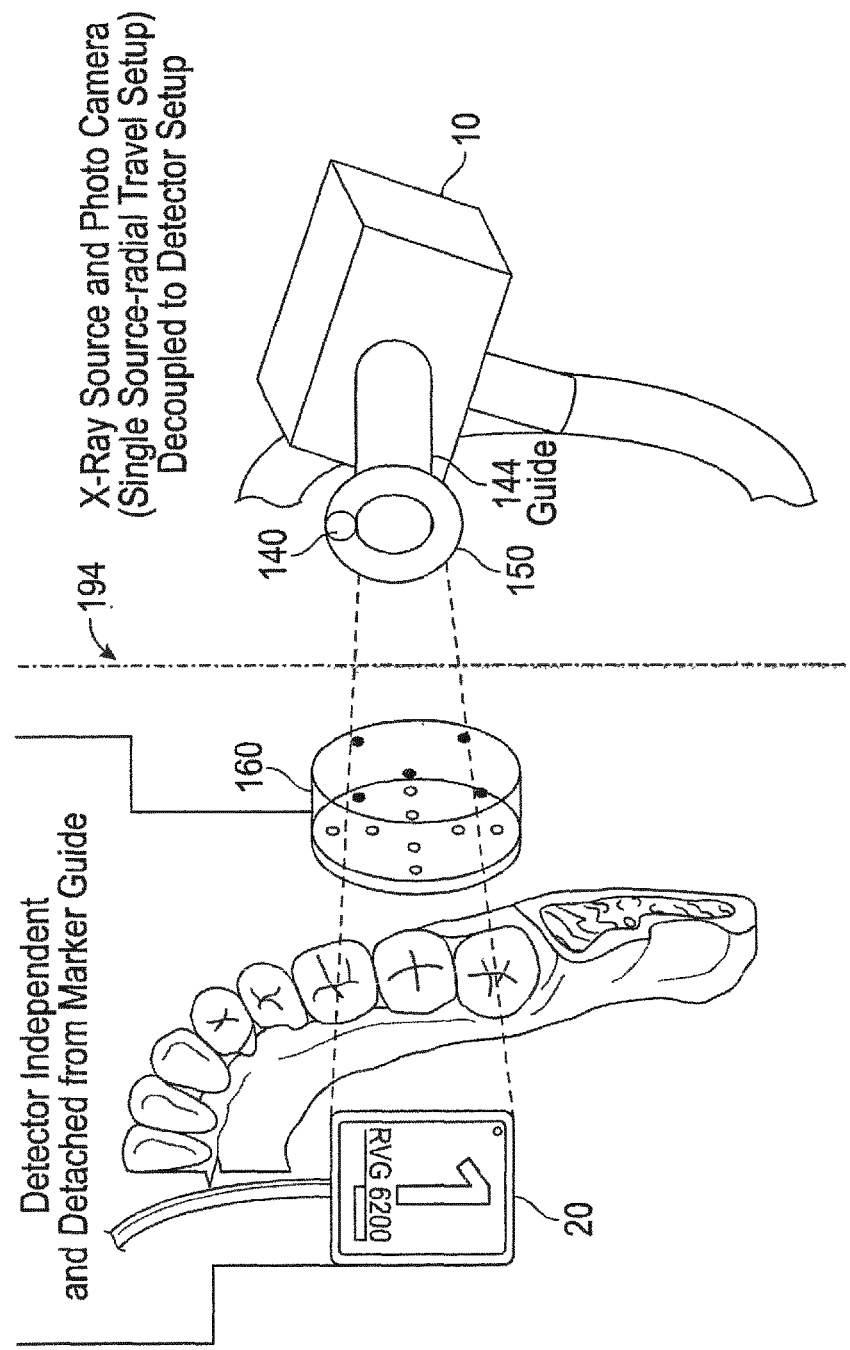
FIG. 12B is a schematic diagram that shows the use of a marker guide that is not directly coupled with the intraoral detector.

The schematic diagram of FIG. 12A shows the use of exemplary marker guide embodiments 160 that is coupled with intraoral detector 20 through frame 78. Marker guide 160, described in more detail herein, provides a number of functions that assist in alignment and collimation for the x-ray source 10 and relate the spatial position of the intraoral x-ray detector to the position of x-ray source 10. FIG. 12B shows a configuration with marker guide 160 un-coupled from detector 20.

When using radio-opaque markers, the location of the source relative to the detector can be determined from image content, preferably around the edge of the FOV. The collimator and detector can be mechanically uncoupled with these markers provided in the radiation field and appearing in image content. When using radio-transparent optical markers, the collimator and sensor must be mechanically coupled or have some type of sensed positioning. Alternatively, optical markers can have an 3D orientation that allows the location of the source relative to the detector can be determined from camera, reflectance or optical image content, which can be sequentially or simultaneously obtained relative to the x-ray image content.

FIG. 13A shows an exemplary treatment system 164 embodiment with chair and other apparatus for dental procedures. Frame 78 that houses marker guide 160 and provides a secondary collimator 56 supported from a mount 162 on system 164 such as from a base 198 or from the dental chair. Alternately, collimator 56 or its supporting frame can be mounted by a support extending from the ceiling. This arrangement, with mounting to stabilize collimator 56 position without requiring the device to be held by the patient, helps not only to support the weight of frame 78 that provides the secondary collimator, but can also help to provide inherent alignment as well as sensed alignment of x-ray source 10 to the patient and intraoral detector 20. As indicated by the arrow, x-ray source 10 can be moved toward frame 78, so that it is at the proper distance and alignment for the image acquisition sequence.

Frame 78 can be part of a headrest, such as an adjustable headrest, for patient positioning to allow tomosynthesis imaging.

FIG. 13B is a top view schematic diagram that shows positioning of frame 78 with secondary collimator, wherein frame 78 is mounted to an exemplary support embodiment that extends from the dental chair, from the ground or ceiling, or from another nearby support structure external to the patient. An arm 192 or other linkage or coupling device can also be mounted to frame 78 in order to guide positioning and movement of source 10 during tomosynthesis imaging. With this arrangement, source 10 is effectively coupled to the secondary collimator 56 of frame 78. This obviates the need for any type of alignment mechanism for alignment of source 10 to the secondary collimator. This arrangement can be used with radio-opaque or visible markers for indicating the relative position of the detector.

One or more sensors 152, such as an accelerometer or electromagnetic device such as a Hall sensor can be provided to detect movement and positioning of frame 78 on mount 162, helping to determine accurate registration of marker guide 160 relative to detector 20 and to x-ray source 10.

Marker Guide Composition

Figure 14A:
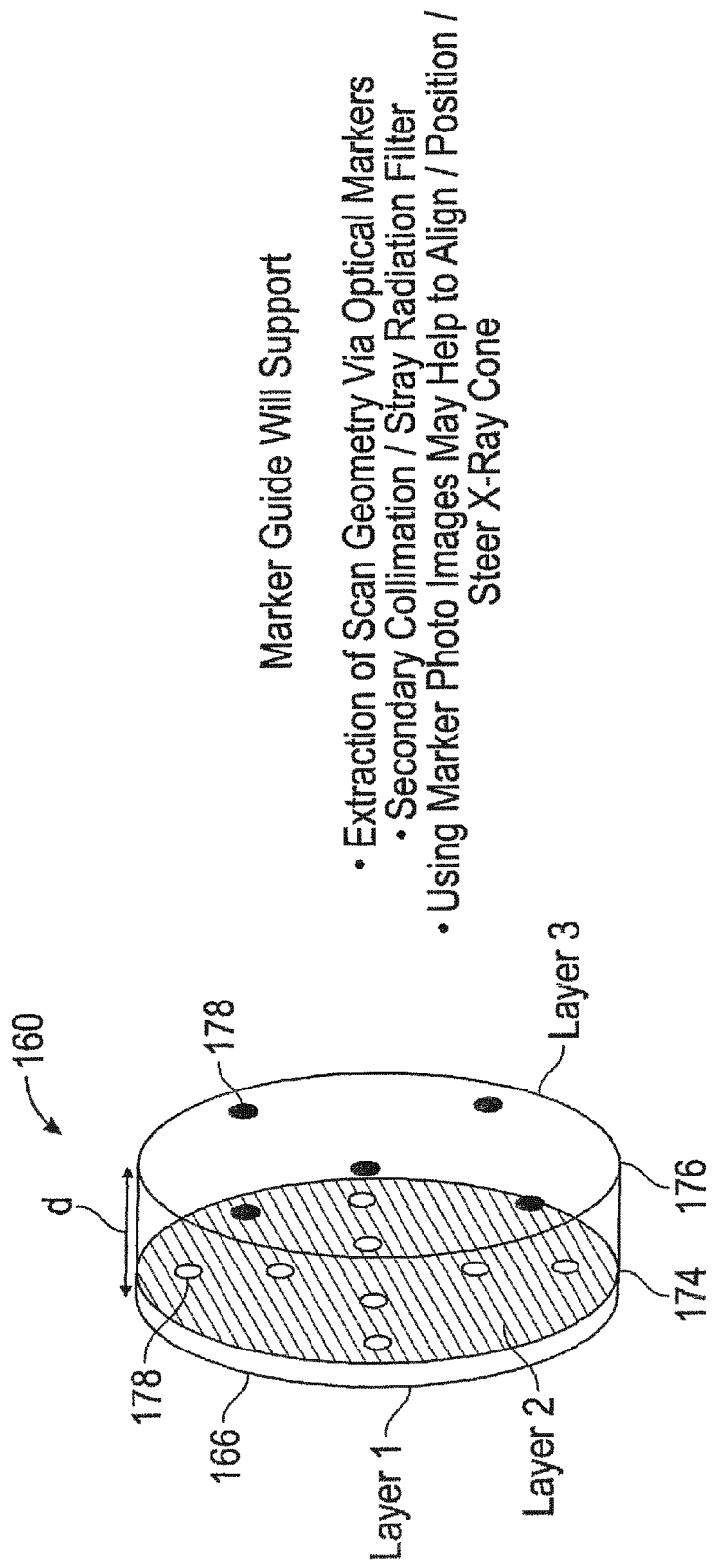
FIGS. 14A and 14B show the assembly and components of a marker guide for alignment according to an exemplary embodiment according to the application.
Figure 14B:
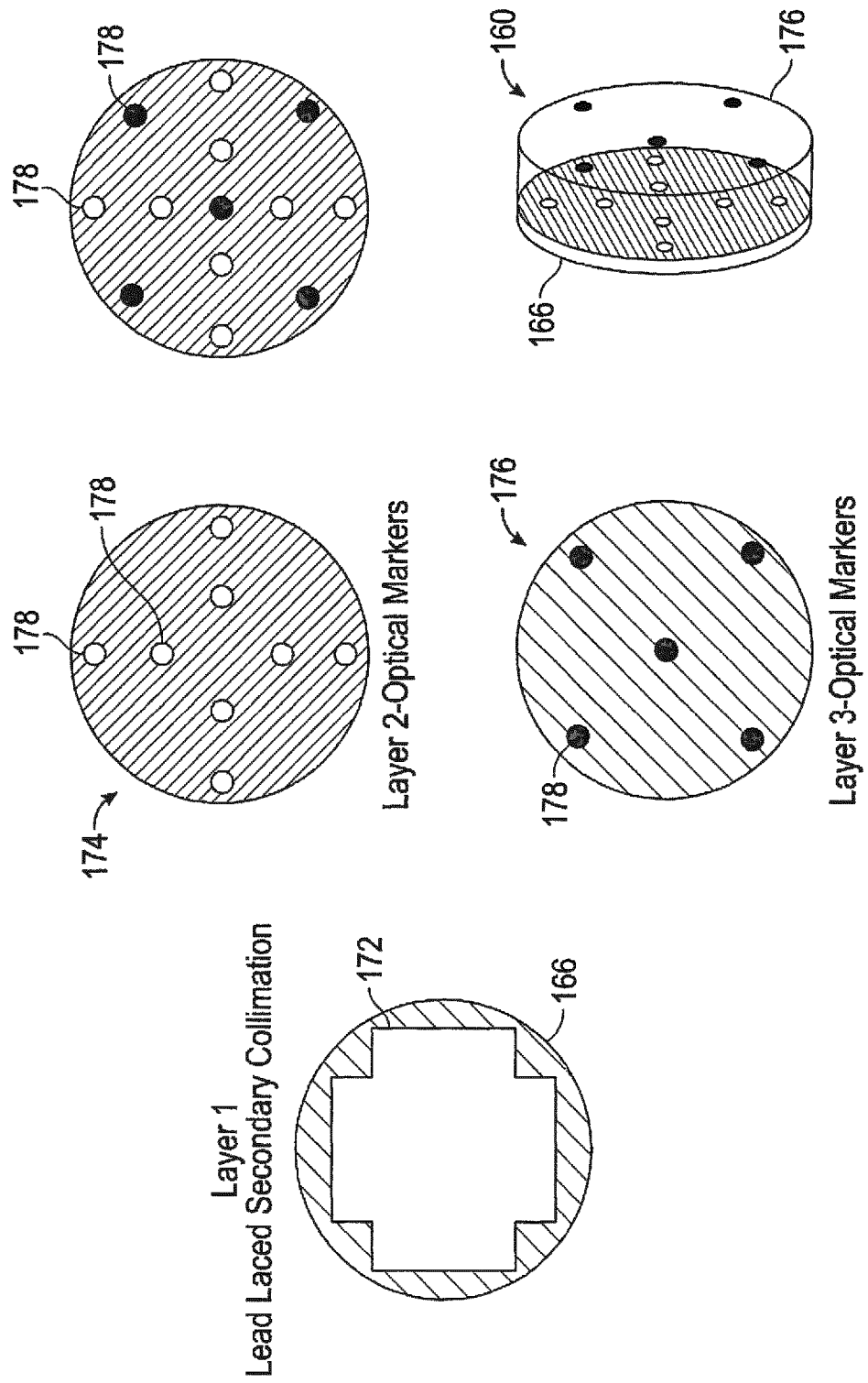

FIGS. 14A and 14B show the assembly and components of marker guide 160 according to exemplary method and/or apparatus embodiments of the present disclosure. FIG. 14A shows exemplary marker guide 160 as assembled. FIG. 14B shows layered components for forming marker guide 160. A collimation layer 166 serves as a secondary collimator for the incident x-ray beam, held substantially against the face of the patient and providing a window 172 framed with radio-opaque shielding for localized collimation. The shielding can be provided by lead-laced material, for example. Layer 2 174 and layer 3 176 provide optical markers 178 for assisting in extraction of scan geometry for alignment. Separation of layers 174, 176 by a distance d helps to facilitate alignment measurement. Markers 178 have an overlaid arrangement shown in FIG. 14B and can be sensed by camera 140, with the resulting image processed for obtaining alignment data. Markers 178 can be different shapes (e.g., non-symmetric), layers, 3D configurations, or colors to support alignment detection. One or more of markers 178 can alternately be radio-opaque.

Figure 15:
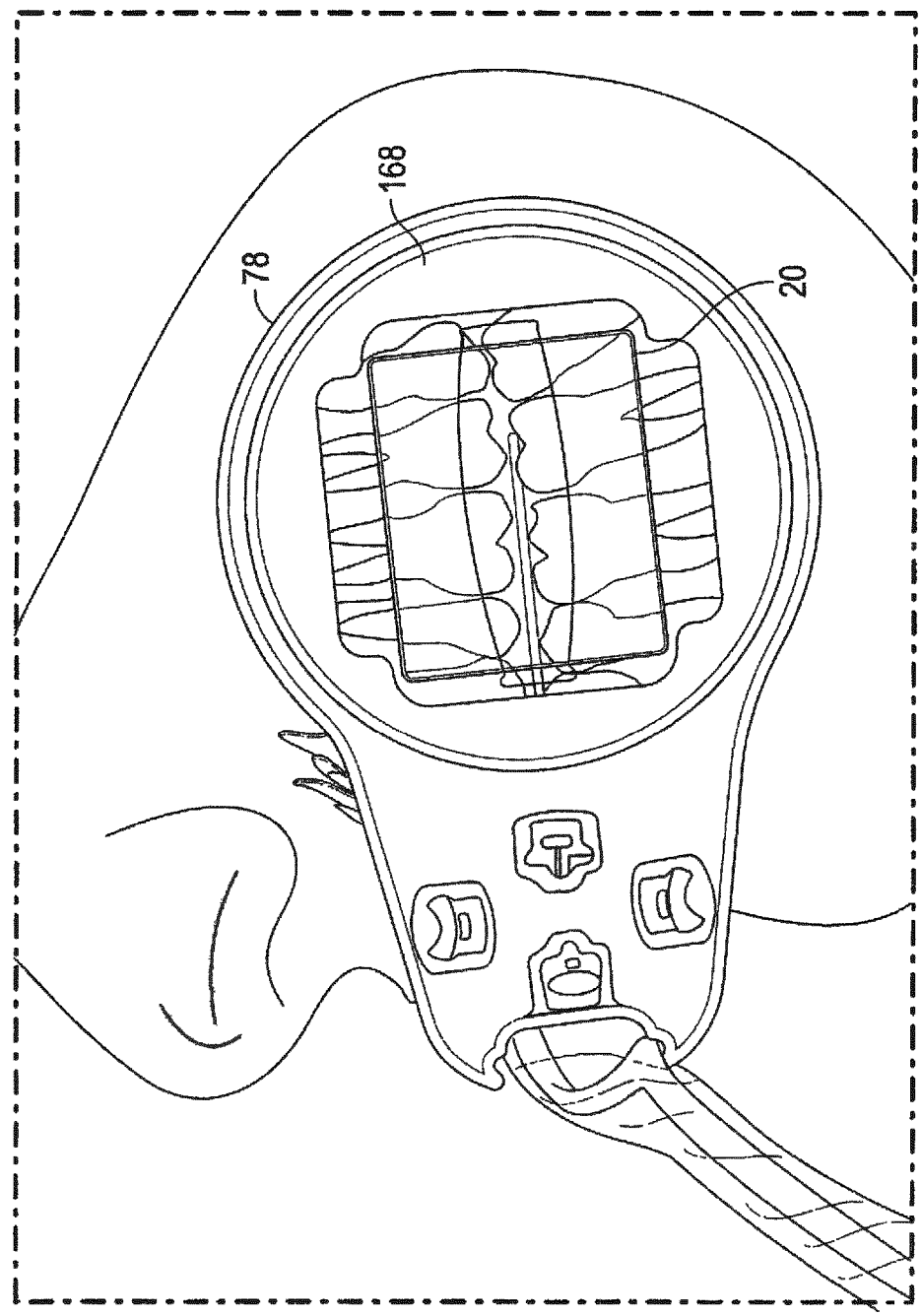
FIG. 15 shows position of a frame against the patient's face for alignment and collimation support.

Shown in position against the patient's face in FIG. 15, frame 78 has a support structure for proper alignment of collimation layer 166 of marker guide 160 relative to frame 78 (FIGS. 14A, 14B, 15). FIG. 15 also shows the position of intraoral detector 20 suitably positioned with respect to frame 78.

Figure 16:
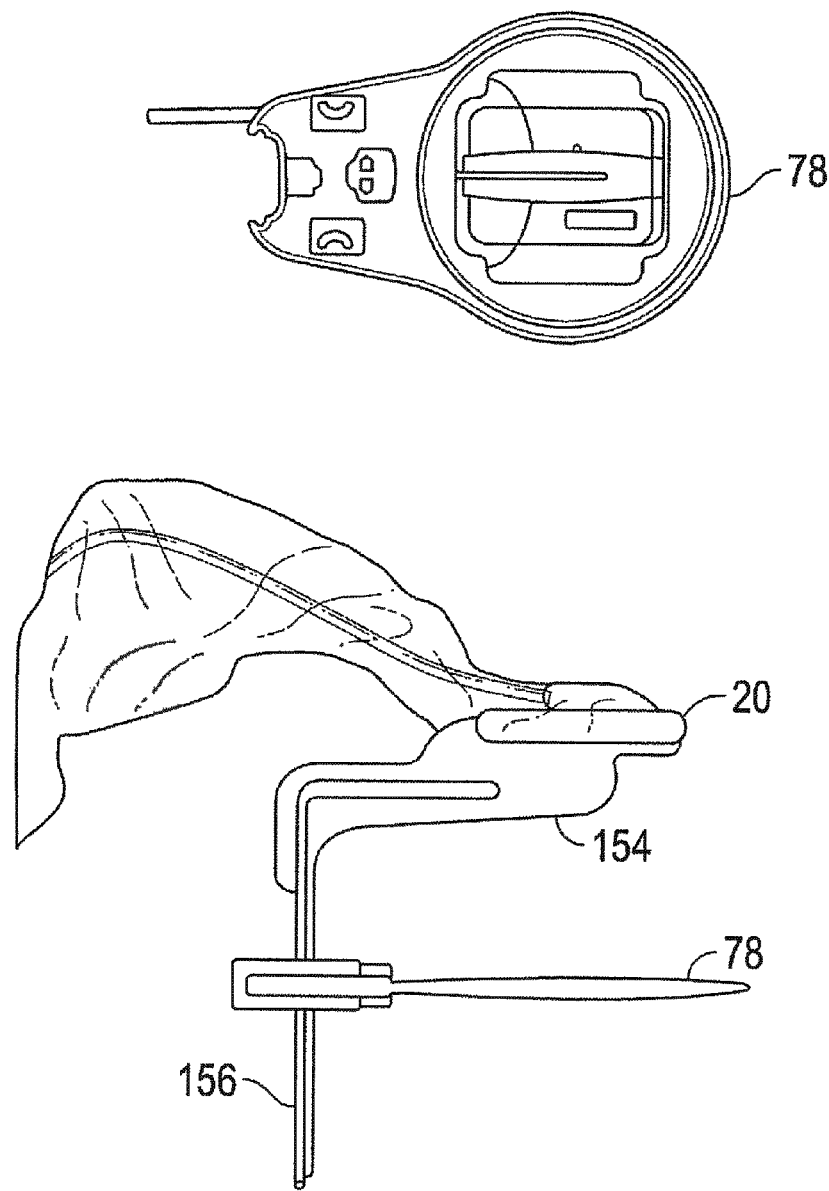
FIG. 16 shows side and top views of a frame for collimation and alignment and associated components.

FIG. 16 shows side and top views of frame 78 and associated components. A bite block 154 helps to stabilize the position of detector 20 within the mouth. An adjustable rod 156 allows positioning of the bite block 154 and detector 20 to suit the patient's comfort.

It should be noted that frame 78 and its associated marker components can be used with a single-source x-ray source 10 or with an array of x-ray sources, such as that provided using a Spindt-type field emitter based x-ray source for example.

Figure 17:
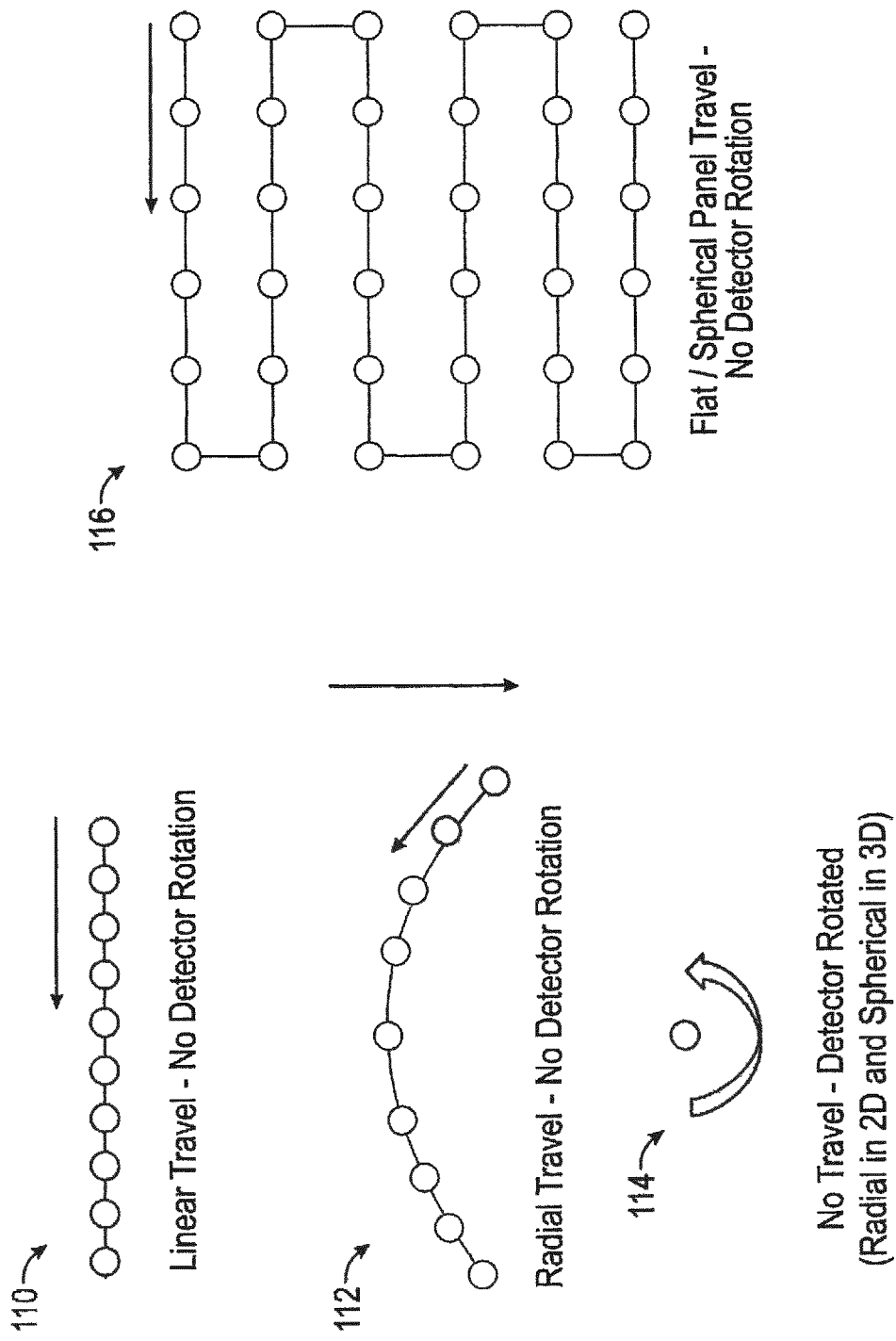
FIG. 17 is a schematic diagram showing exemplary relative travel paths that can be traced relative to the imaged subject for tomosynthesis imaging.

The schematic diagram of FIG. 17 shows exemplary relative travel paths that can be traced relative to the imaged subject for tomosynthesis imaging. A linear travel path 110 or radial travel path 112 can be provided without detector rotation. In travel path 114, the source remains in position while the director rotates. In travel path 116, flat or spherical source travel is provided, without detector rotation. For any of travel paths 110, 112, and 116, relative movement can be provided by successively energizing individual sources of an array, such as a CNT source array, for example.

It can be appreciated that control logic processor 26 obtains and stores both image data and positional information when performing tomosynthesis imaging. As each image is obtained, control logic processor 26 stores the image data and corresponding information about the relative spatial position of the energized x-ray source and detector 20. Position data and image data can be stored as part of the same data structure, such as in the image data file, or may be stored in separate data structures, such as in separate files or database locations. In one embodiment, control logic processor 26, then optionally provides information that indicates a recommended positional adjustment for the x-ray source for obtaining the next x-ray image at the next spatial position and the next angular orientation. This information on recommended positional adjustment can be provided in a number of ways, including displayed information on display 28 (FIG. 5), using an audible cue, or by providing graphical guidance to the operator in order to set up the next exposure, which can be in the form of projected image content and format, such as by projecting instructions or target information onto the cheek of the patient, for example. Relative positional information related to each image is stored in some form and used by image processing logic on control logic processor 26 in order to generate the volume image.

Use of Spindt-Type Field Emitter Based or Other Radiation Source Array

Figure 18:
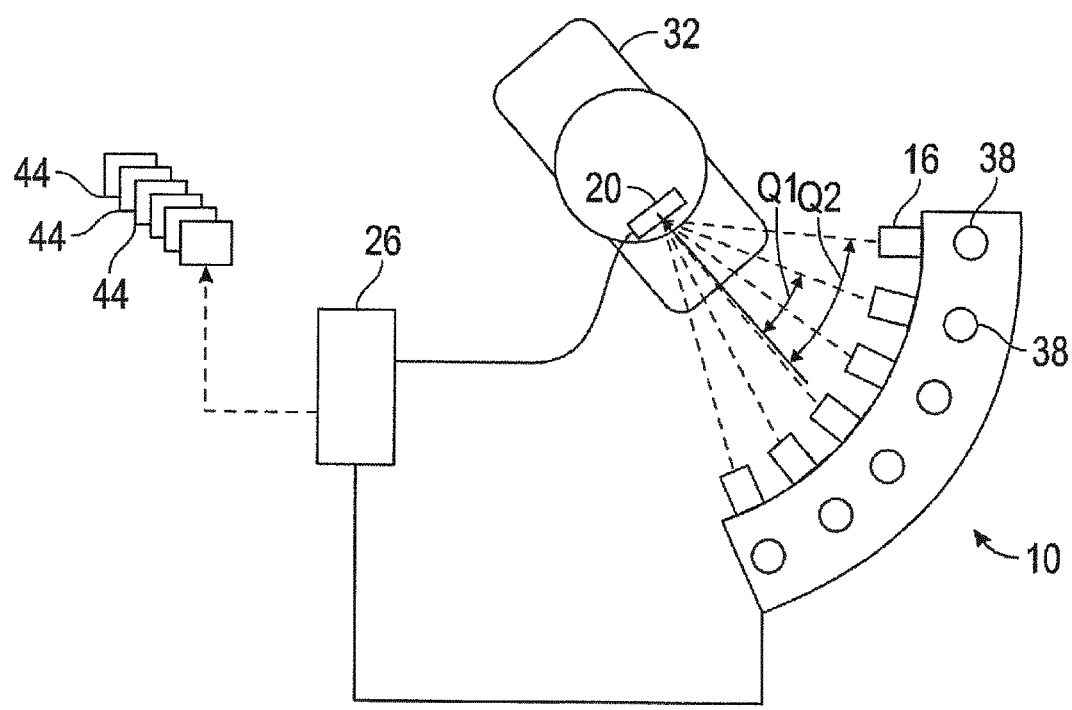
FIG. 18 is a schematic block diagram view that shows a Spindt-type field emitter based source or other x-ray source array for image acquisition.

The schematic diagram of FIG. 18 shows the use of a radiation source array as x-ray source 10. Each x-ray source 38 is from a cathode that utilizes Spindt-type field emitters. Using Spindt-type field emitter cathodes, the x-ray sources are stationary or relatively fixed in position with respect to each other within the array; the array itself moves as a single unit. This type of x-ray source is capable of rapid on/off switching on the order of microseconds. Other suitable x-ray sources can include paired pulsed conventional fluoro-capable thermionic sources that are spatially separated. These options provide sufficient x-ray fluence with short exposure times and simultaneously allow exposure sequences without overheating.

According to an exemplary embodiment according to the application, each individual source 38 has its own collimator 16, as in the embodiment shown in FIG. 18, for example.

Alternate Concepts for Relative Movement

Data must be obtained in order to identify the spatial position of detector 20 and the relative spatial position of x-ray source 10 for each image.

According to the alternate exemplary embodiment of FIG. 13B, described previously, x-ray source 10 is coupled to frame 78 by pivoting arm 192 that serves as a support and guide for source 10 movement in a curved or arcuate path. This arrangement allows source 10 movement over a well-defined angular track, simplifying design of transport apparatus for source 10 movement and further simplifying collimation design.

Figure 19:
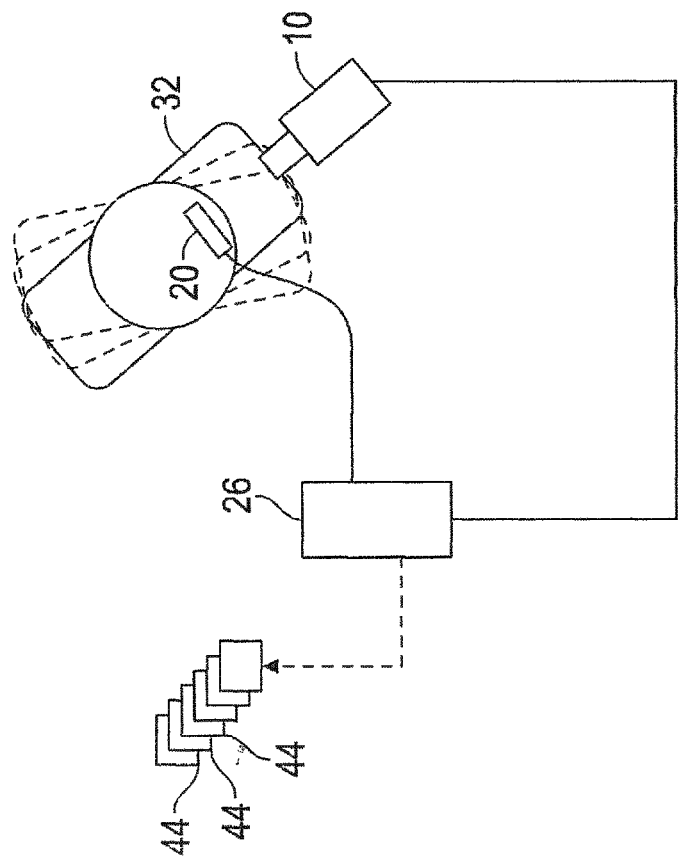
FIG. 19 is a schematic block diagram that shows an imaging pattern used for obtaining a volume image from a limited number of x-rays in an alternate embodiment.

In the alternate exemplary embodiment of FIG. 19, x-ray source 10 is fixed in place and patient 32 is rotated, such as by incrementally rotating a treatment chair for example, to shift from one exposure angular orientation to the next. Again, relative positional information for both detector 20 and x-ray source 10 must be established and stored for each component image by control logic processor 26 or a related processing device.

Image Acquisition Process

Figure 20:
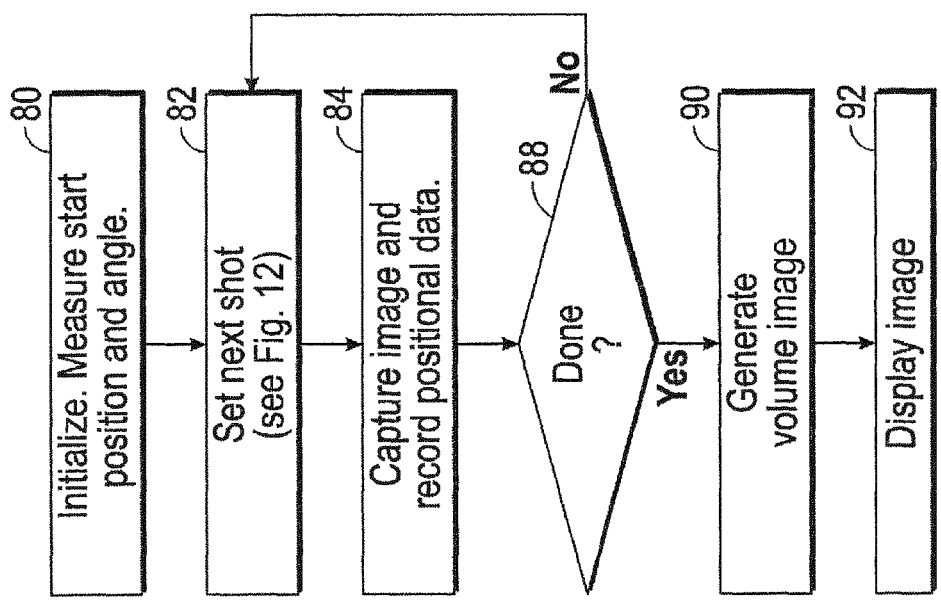
FIG. 20 is a logic flow diagram that shows a sequence for capturing x-ray images to generate a volume image.

The logic flow diagram of FIG. 20 shows a sequence of steps for obtaining a series of component images in one exemplary embodiment. An initialization step 80 begins the sequence and obtains data on the initial start position and angle. In one embodiment, initialization step 80 also sets up or calculates the number of images to be obtained and, for each image, its corresponding exposure angle. This information may be fixed or variable, and may be calculated using control logic processor 26 or entered by the dentist or technician using setup software that is in communication with control logic processor 26. Detector 20 is securely positioned in the patient's mouth and the needed source-detector alignment is at least coarsely made by the technician. In a setup step 82, imaging apparatus 22 provides the needed image display, projected onto the face or head of the patient, to help guide alignment and aim of x-ray source 10, as was described earlier with reference to FIGS. 7A and 7B. In one embodiment, the image content that is projected onto a portion of the patient changes according to the relative accuracy of the angular orientation. This can be a change in color, intensity, blinking, or other attribute of the projected content. It should be noted that the display may provide a hint or suggestion of the best position for each subsequent radiographic image capture. However, it is important that the actual spatial position be accurately measured and recorded in order for proper execution of the limited-angle volume imaging algorithms.

Continuing with the logic flow of FIG. 20, each component image is obtained in an image capture step 84, and the image stored along with information about the actual measured spatial position and the angular orientation at which the exposure was obtained. A decision step 88 checks to determine whether or not all component images needed according to initialization step 80 have been obtained and loops back to setup step 82 when subsequent images are needed. At the conclusion of this processing for image capture, a volume image generation step 90 is executed in order to generate the resulting composite volume image obtained from this sequence. A display step 92 then displays the volume image that has been generated.

FIG. 21 is a block diagram showing spatial position and angular orientation associated with the image data for each component image 44 in the set of images that is obtained. In the exemplary embodiment shown, a spatial position data field 50 and an angular orientation data field 52 are stored along with x-ray image data 54, such as by storing the measured position and angle geometry in a header portion of the x-ray image data file. Alternately, spatial position and angular orientation data can be separately stored, linked or otherwise associated with the image data. This information is needed for proper reconstruction of the volume image.

FIG. 22 is a logic flow diagram that shows optional system activity within image setup step 82 of FIG. 20 in preparation for each image capture in a sequence. A calculation step 60 uses position coordinate and angular orientation data from the x-ray system or stored with the previous image and calculates a next position and angular orientation for relative movement of x-ray source 10 and/or detector 20. An optional target projection step 62 then projects an image onto the patient, wherein the image is indicative of positional adjustment and angular adjustment that is needed between x-ray source 10 and detector 20 for obtaining a next x-ray image at the next spatial position and angular orientation. As noted earlier, the optional projected display can indicate the needed adjustment using color, blinking or other effects, numeric values, directional indicators or icons, such as an arrow, or other visual effects. Then, in a looping operation, a reassessment step 64 periodically readjusts the projected display according to measured changes in positional adjustment and angle that have been made by the technician. When adjustment is correct to within some predetermined tolerance, a correct adjustment display step 66 then executes, indicating that the adjustment is acceptable for obtaining the next image.

Given the information that is available on relative position when using the component arrangement shown in FIGS. 9A-11, an exemplary embodiment of the present invention uses continual re-calculation and repeated checks of sensors and other position-sensing components for correction of, and adapting to, minor position changes and patient movement. With this arrangement, it is not necessary that detector 20 and x-ray source 10 have fixed, predetermined positions relative to each other or achieve precisely those positions calculated for the next image. However, in any case, detector 20 must have a fixed spatial position relative to the teeth or other objects being imaged. Programmed image processing logic can adapt to changes in position that are within a reasonable range of angles, for example. In one embodiment, one or more additional position sensors at fixed spatial positions are used to establish reference points for angular and positional orientation. In addition, automated detection and correction of patient motion artifacts can also be performed, using image processing techniques known to those skilled in the image acquisition arts.

The limited-angle volume image that is formed from two or more component x-ray images provides some measure of volume-related information for the tooth or other imaged structure. Advantageously, this is provided without the higher levels of exposure needed for full CBCT imaging and without the need for specialized CBCT gantry and related equipment. Positional information that is obtained using sensor 24 and detectable elements 30 is used by 3-D image reconstruction algorithms to generate a corresponding volume image that includes a tooth or other feature and to populate voxels within that volume image with suitable data values. The volume image can be formed without requiring the complex filtered back-projection algorithms that are typically used for CBCT reconstruction, for example. Images obtained can be viewed on a conventional display monitor or may be viewed using a stereoscopic viewing apparatus, for example. The needed volume image can be generated dynamically according to a preferred viewing angle indicated by the practitioner, for example.

Variations in the Image Acquisition Sequence

According to an exemplary embodiment according to the application, the image acquisition sequence can be varied in order to obtain one or more images under different conditions. For example, over a series of images taken under tomosynthesis conditions and angles, one or more images can be captured under different conditions, such as using settings typically applied for conventional 2-D radiography imaging. This can be, for example, a central image in a sequence, such as the 10th or 11th image in a series of 20 tomosynthesis image captures. Different capture conditions, including exposure settings, binning, dual-energy and other parameters can be used for images acquired in this manner.

Where one or more images are obtained under different conditions, features such as higher fidelity and sharpness of these images can be used to improve image content for other images in the series.

Detector Binning

Binning methods can be used to help speed image acquisition. Binning groups sets of adjacent pixels together in order to speed image data access and data refresh cycles. Binning is typically done in a symmetrical pattern, such as 2×2 binning, 3×3 binning, etc. However, binning can also be performed in one direction, such as 2×1 binning, for example. Non-symmetric binning can be useful for volume imaging, with binning in the direction parallel to relative motion of the x-ray focal point different from binning in orthogonal directions.

Radioscopy

Radioscopy imaging methods, including fluoroscopy for example, obtain images of the subject in rapid succession and provide a continuous view of the subject that can have a video appearance. In radioscopy, volume reconstruction is not provided; instead, the sequence of acquired radiographic images displays. There is no relative movement between the x-ray source and the detector in radioscopy; the same source-to-detector geometry applies for each acquired image.

Radioscopy can be a useful tool for the practitioner, providing a progressive or "real-time" presentation of a region of interest, such as one or more teeth or a portion of a dental arch, for example. Radioscopic presentation can be combined with visualization software that indicates drill angles or other features that are helpful during a procedure. Radioscopy acquisition takes advantage of a high speed digital detector having good resolution.

In general, radioscopy has an acquisition time similar to that needed for tomosynthesis, but with somewhat longer x-ray exposure time. There can be a tradeoff of spatial resolution vs. dose for radioscopy acquisition.

Dual Energy Imaging

Certain exemplary method and/or apparatus dual-energy imaging embodiments allow advantages of improved ability to analyze different types of tissue that are found in the imaged anatomy. Dual energy or multispectral imaging can be obtained using a photon-counting detector having multiple thresholds, as described previously with reference to FIG. 2B. Alternately, other detector arrangements can be used.

Dual energy (DE) imaging has been used as an alternative method for reducing noise content and differentiating various types of imaged anatomy. In conventional DE imaging, low and high kVp exposures of the same anatomy follow each other in close succession, so that their results can readily be combined without requiring extensive registration techniques. This can help with subsequent segmentation of bone features, for example, allowing more accurate interpretation of the x-ray image content. For tomosynthesis and 3D volume imaging overall, such as provided by CBCT and CT apparatus, there can be significant advantages in providing dual-energy image content for reconstruction and subsequent analysis.

Dual energy tomosynthesis allows different structures to be reconstructed from the same imaged tissue.

Exposure technique settings can be varied from one projection image to the next during image acquisition.

Reconstruction

Control logic processor 26 or an associated processor or other computer used for image processing can execute any of a number of known techniques for limited-angle tomosynthesis reconstruction, familiar to those skilled in the 3-D imaging arts. For example, in an article entitled "A comparative study of limited-angle cone-beam reconstruction methods for breast tomosynthesis", *Med. Phys.* October 2006; 33(10): pp. 3781-3795, authors Zhang et al. describe a number of reconstruction algorithms used to solve a similar type of problem in limited-angle mammographic imaging, including back-projection, algebraic reconstruction, and probabilistic techniques. The Siltanen et al. '241 patent noted earlier describes a 3-D reconstruction method from sparse 2-D image data using modeling data for tooth structures. The Kalke '7801 application noted earlier describes another method for tooth image reconstruction using a frequency transform. Other reconstruction methods for 3-D imaging could alternately be employed.

Among its advantages, a volume image can be formed for viewing image slices from different angles, depending on how much component image data is available. Where a sufficient number of component 2-D projection images are obtained at different relative angles, the resulting volume image can be formed and displayed from multiple view angles, thus assisting the dental practitioner in making a more accurate diagnostic assessment of a tooth or other structure.

Presentation/GUI

The operator can have the capability to set up the operating mode of the imaging system using operator interface commands.

Figure 23:
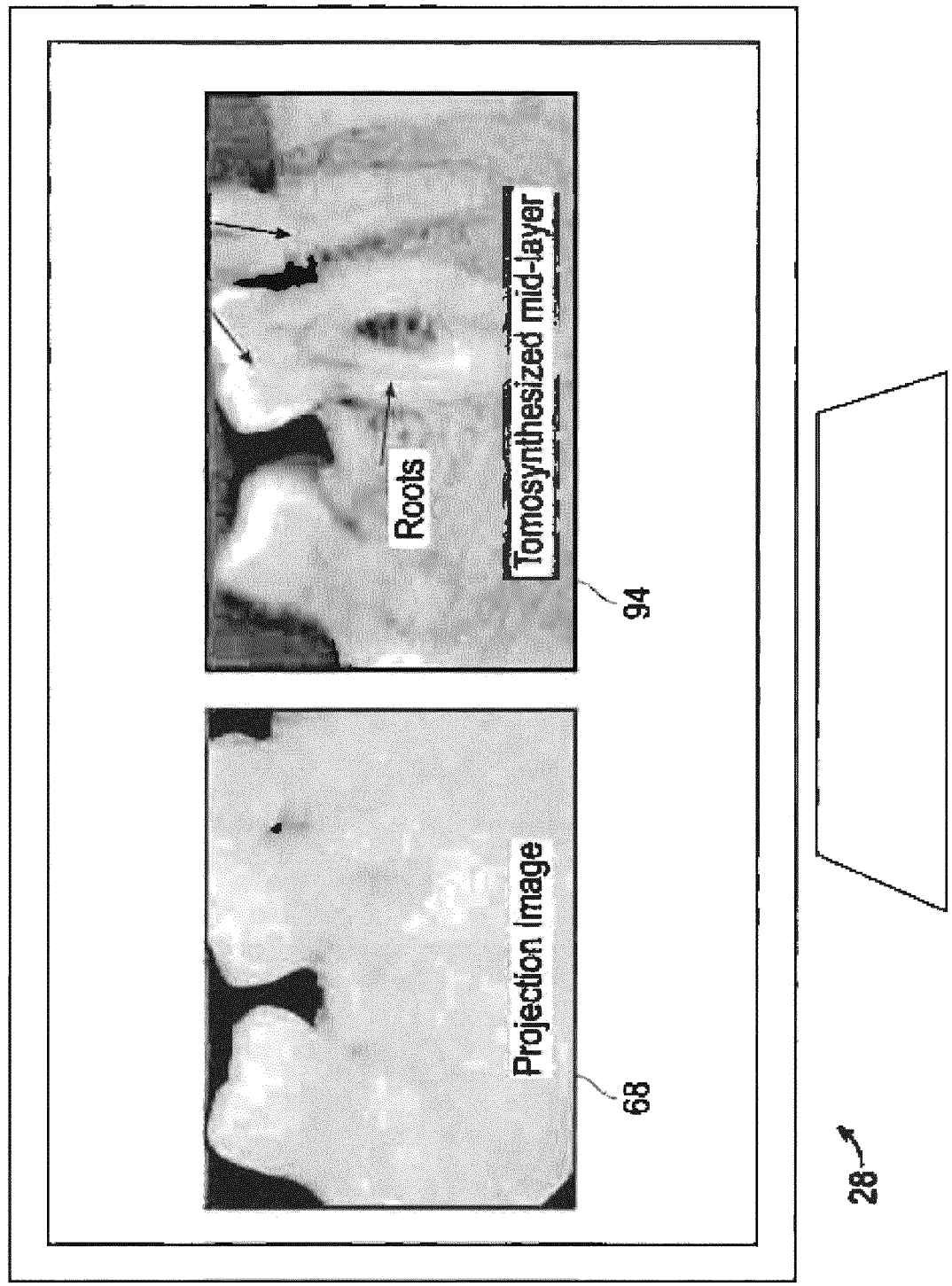
FIG. 23 shows a comparative display for a projection image and a tomosynthesis image slice.

According to an exemplary embodiment according to the application, the operator interface on display 28 (FIG. 1) can show any subset of the projection images that have been obtained as part of the tomosynthesis series, as well as showing any suitable tomosynthesis slice from the reconstructed image data. FIG. 23 shows display 28 having a comparative display that shows a 2-D projection image 68 alongside a corresponding tomosynthesis slice 94.

Geometric Calibration

Geometric calibration helps to provide improved accuracy and resolution for tomosynthesis reconstruction. Embodiments of the present disclosure provide a number of solutions for geometric calibration suitable for chair-side dental tomosynthesis.

Detector Attachment with Markers

Figure 24A:
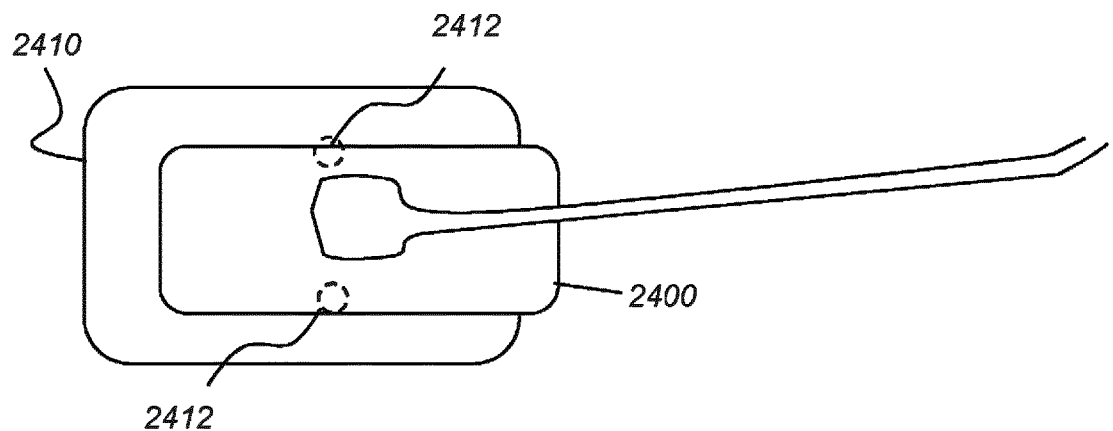
FIGS. 24A and 24B show alternative embodiments of an intraoral detector having markers within a defined imaging area.
Figure 24B:
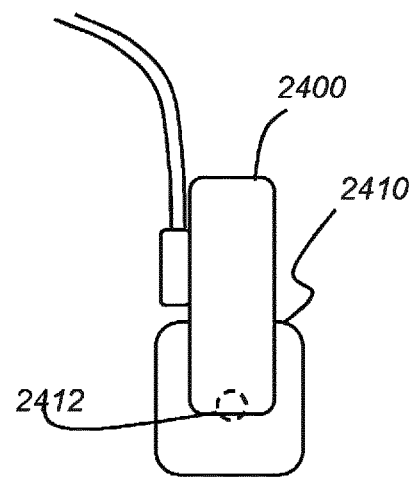

According to an embodiment of the present disclosure, as shown in FIGS. 24A and 24B, one or more radio-opaque markers 2412 are provided on a detector attachment 2410 that is coupled with intraoral detector 2400. Preferably, markers 2412 are disposed within the imaging area of detector 2400, disposed at or near the center of the imaging area or arranged symmetrically about the center of the imaging area. With this centered arrangement, markers 2412 lie within the imaging area in each projection image. The markers 2412 are configured to condition acquired x-ray images to relate the spatial position of the intraoral x-ray detector to the x-ray source position Markers 2412 can be formed of any of a number of suitable materials for intraoral use. Non-toxic materials that can be appropriate for intraoral imaging can include chromium steel, ceramic, tungsten carbide, and gold, for example. Markers 2412 can be spherical. A suitable size range for tomosynthesis imaging is 0.5 mm diameter. Other sizes and shapes can be used as desired.

According to an embodiment of the present disclosure, materials that are radio-opaque with atomic numbers of 45 or below are used. Exemplary materials of this type include chromium steel (with atomic number 26) and ZrO2 ceramic material (with atomic number 40). Materials having opacity in this range tend to generate correspondingly lower intensity imaging artifacts than do materials that exhibit higher attenuation to radiation.

The markers 2412 appear in each image of the tomosynthesis series. Given the well-defined marker 2412 placement on the detector and knowing the source path of the incident radiation for tomosynthesis, the acquired 2-D projection images can be geometrically aligned for accurate reconstruction.

Image processing techniques can be applied in order to compensate for marker appearance and obstruction caused by the marker. Techniques such as inpainting and interpolation can be used to remove the marker(s) from one or more of the projection images, thereby helping to minimize or eliminate metal artifacts, for example.

Holder-Mounted Phantom

Figure 25:
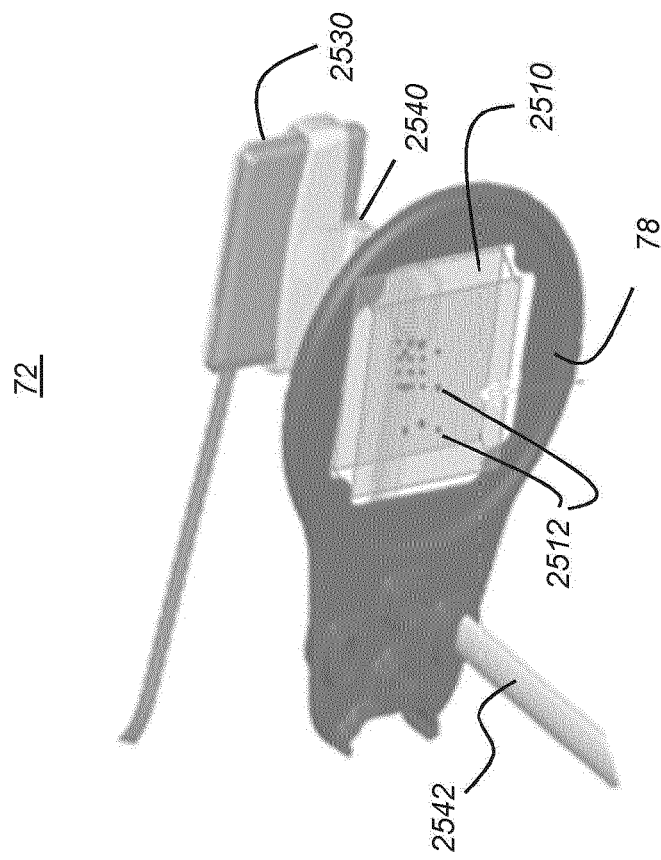
FIG. 25 shows a calibration phantom that is provided as an integral part of a detector holder.

An alternate type of detector attachment can be used for geometric calibration for tomosynthesis images obtained during surgery or other treatment procedures. FIG. 25 shows a calibration phantom 2510 that is provided as an integral part of detector holder 72 and held in place on frame 78, along the path of radiation to a detector 2530. Phantom 2510, shown in different shapes in FIGS. 26A and 26B, can be held in place near the patient's cheek, with the help of a bite block 2540 that connects between detector 2530 and frame 78. This arrangement helps to provide a fixed and measurable geometric relationship between markers 2512 on phantom 2510 and detector 2530. An optional stick 2542 can assist the practitioner or technician in preparatory positioning of the detector 2530 and phantom 2510. Stick 2542 can have graduated markings to indicate distance between detector 2530 and phantom 2510.

Markers 2512 on phantom 2510 can be provided on two layers, with the layers separated from each other by a distance such as 9 to 11 mm. The layers can form parallel planes, with each plane having an arrangement of markers. By using multiple markers 2512 having a layered arrangement, an embodiment of the present disclosure can use phantom data to more accurately determine the geometry of the imaging process for a given patient.

Markers 2512 can be of the same radio-opaque materials. Although markers 2512 of high density can be used, it can be advantageous to avoid highly dense materials for forming markers, particularly where individual projection images are viewed. According to an embodiment of the present disclosure, for example, materials having atomic numbers of 45 or lower are used for markers 2512, as described previously. Other embodiments can use markers having higher atomic numbers, such as gold and silver, for example. The markers can be encased within phantom 2510, such as encased or embedded in plastic.

Figure 26A:
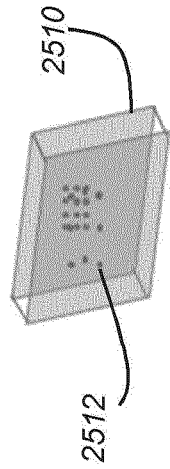
FIGS. 26A and 26B show representative calibration phantoms of different shapes.
Figure 26B:
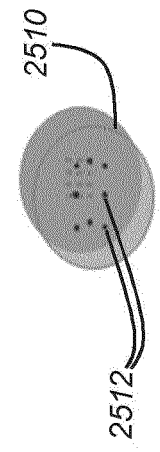
Figure 27A:
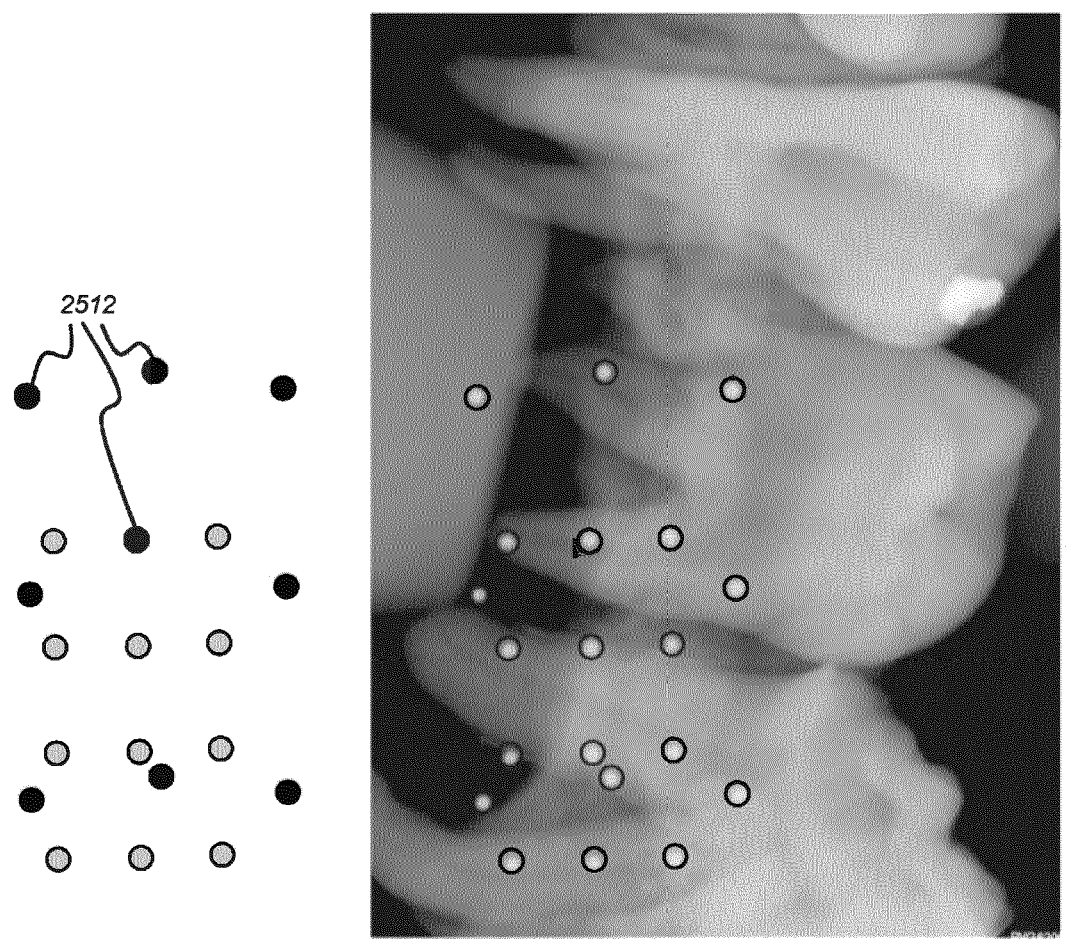

FIGS. 27A, 27B, and 27C show selected 2D projection images of a few representative teeth from a tomosynthesis series using markers 2512 that are arranged in two layers as described with reference to FIGS. 25, 26A, and 26B. As can be seen from this series, the relative positions of the two sets of markers 2512, represented in different grayscale tones in FIGS. 27A, 27B, and 27C according to layer, change according to corresponding positions of the x-ray source relative to the teeth. This change in angular positioning, as shown in the 2D projection image content, enables straightforward computation of the acquisition geometry for each successive image.

According to an alternate embodiment, markers 2512 positioned in different layers have correspondingly different size or density. This arrangement can simplify analysis of the pattern formed by the markers 2512 on the acquired image. With respect to the example of FIGS. 27A, 27B, and 27C, for example, the markers indicated in black can be formed of gold or tungsten carbide (atomic numbers 79 and 74, respectively); markers shown in gray can be ZrO2 (atomic number 40) or other material of lower density than 79 or 74.

Clip-On Phantom

Figure 28:
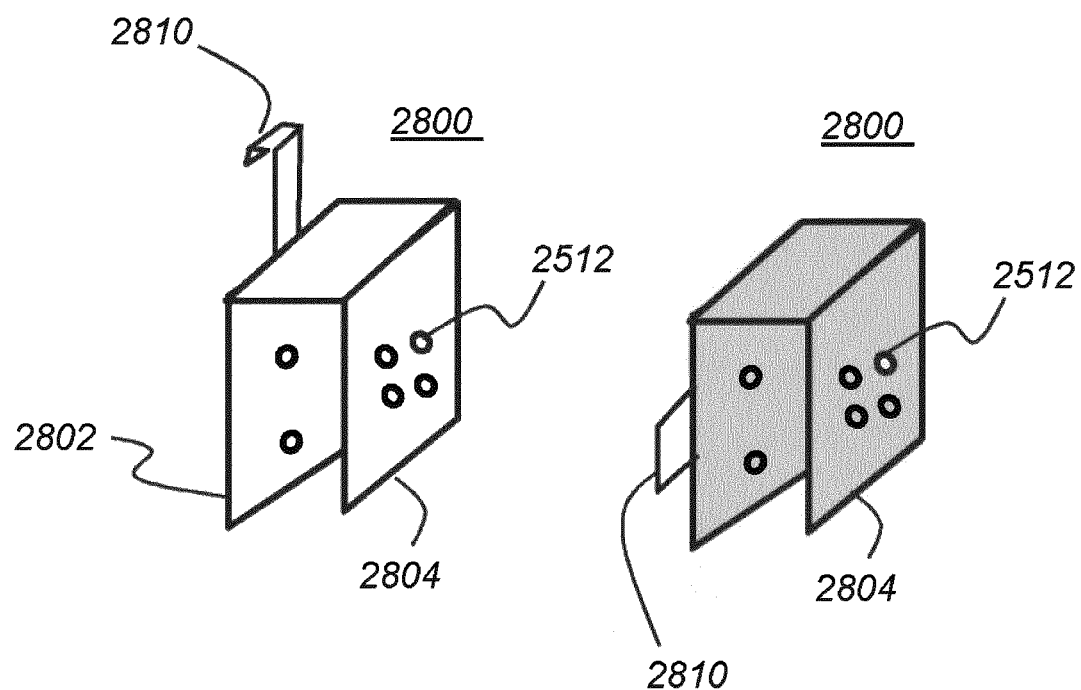
FIG. 28 is a perspective view that shows a pair of clip-on phantoms that slip onto the teeth and provide an arrangement of markers along parallel planes.

For some tomosynthesis imaging applications, it can be helpful to provide a device for holding the detector in position as well as providing markers for facilitating geometric calibration of the acquired images. The perspective view of FIG. 28 shows a pair of clip-on phantoms 2800 that slip onto the teeth and provide an arrangement of markers 2512 along parallel planes. Phantom 2800 can have a distinctive pattern of markers along each side 2802, 2804, respectively proximate buccal and lingual surfaces, for example. A fastener 2810 can also be formed for coupling the detector along one or both sides 2802, 2804 of the clip-on phantom 2800. The coupling can be active, such as using a clamp or other mechanism that engages the detector, or passive, such as having an arm or other member that fits within a sleeve provided on the detector or detector holder. An additional adhesive can be used in order to provide improved stability to the coupling. Adhesive material can also be used for holding the clip-on phantom 2800 in position on the teeth.

Figure 29B:
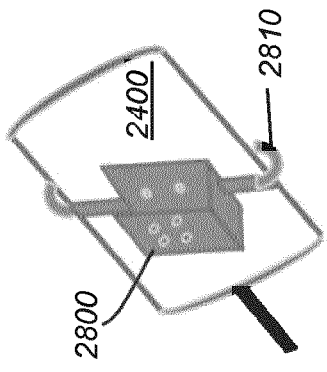
FIGS. 29A, 29B, and 29C are perspective views that show the detector coupled to a clip-on phantom.
Figure 29C:
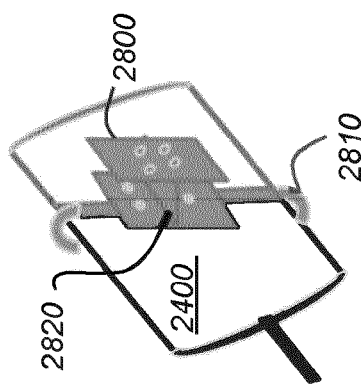
Figure 29A:
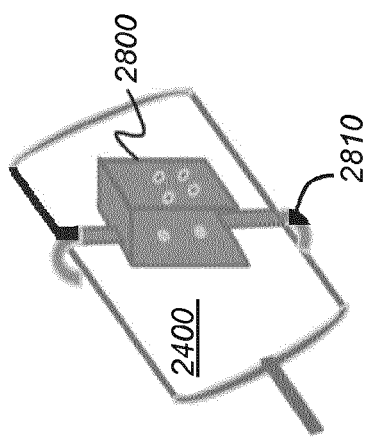

FIGS. 29A, 29B, and 29C are perspective views that show detector 2400 coupled to clip-on phantom 2800. As shown in FIGS. 29A and 29B, phantom 2800 can use lower or upper teeth for support. An embodiment of phantom 2800 shown in FIG. 29C provides a pattern of features that allow the use of both upper and lower teeth for holding detector 2400. A bite plate 2820 is provided between two surfaces that hold the markers. This arrangement can make the FIG. 29C arrangement advantageous for imaging at the bite line.

With respect to the imaging system, phantom 2800 is a holder that provides an arrangement of markers along two parallel planes, enabling markers to be positioned on opposite surfaces of a tooth. The number and arrangement of markers on one plane can differ from the number and arrangement of markers on the other plane. The body of phantom 2800 can be plastic or other radio-transparent material.

Figure 30:
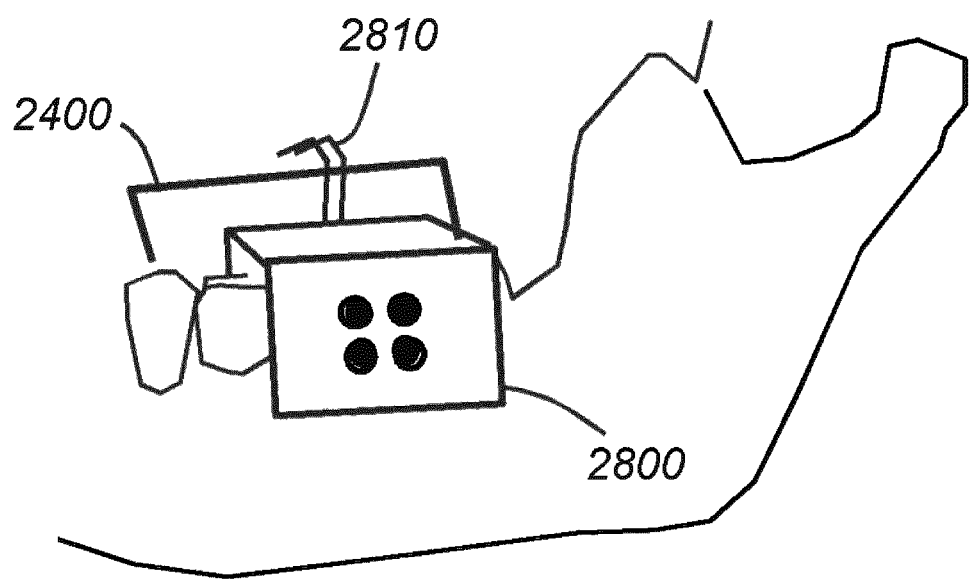
FIG. 30 is a perspective view that shows a phantom in position on a tooth.
Figure 31B:
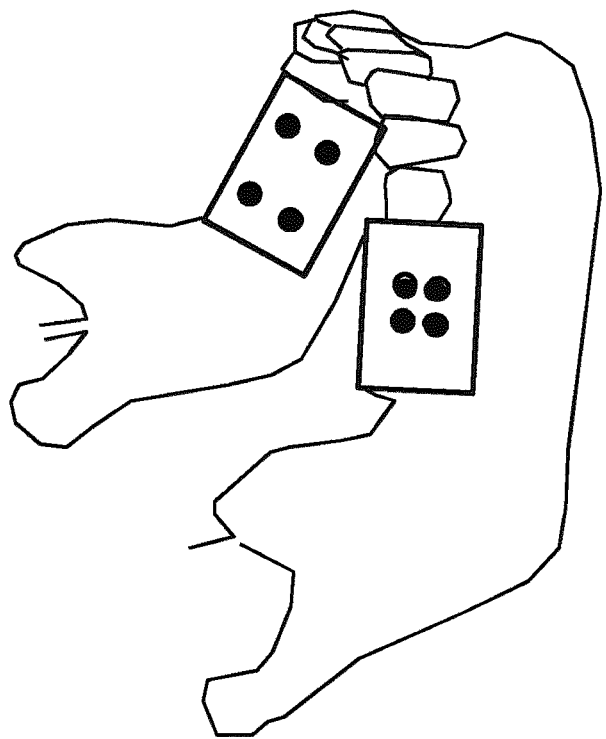
FIGS. 31A and 31B show phantoms from different perspective views in an embodiment with different marker arrangements on buccal and lingual sides.
Figure 31A:
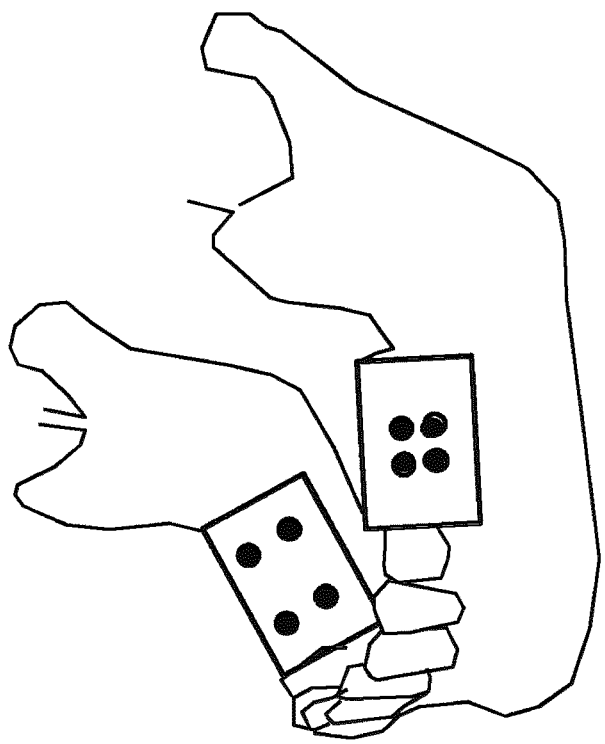

The perspective view of FIG. 30 shows phantom 2800 in position on a tooth and coupled to detector 2400. FIGS. 31A and 31B show phantoms 2800 from different perspective views in an embodiment with different marker 2412 arrangements on buccal and lingual sides.

It can be advantageous to position the detector so that the marker arrangement is centered in the detector imaging area. This allows more efficient calculation and provides improved likelihood of correct angle calculation from the acquired images.

The invention has been described in detail with particular reference to a presently understood exemplary embodiments, but it will be understood that variations and modifications can be effected within the spirit and scope of the invention.

For example, control logic processor 26 can be any of a number of types of logic processing device, including a computer or computer workstation, a dedicated host processor, a microprocessor, logic array, or other device that executes stored program logic instructions.

The presently disclosed exemplary embodiments are therefore considered in all respects to be illustrative and not restrictive. The scope of the invention is indicated by the appended claims, and all changes that come within the meaning and range of equivalents thereof are intended to be embraced therein.

Consistent with at least one exemplary embodiment, exemplary methods/apparatus can use a computer program with stored instructions that perform on image data that is accessed from an electronic memory. As can be appreciated by those skilled in the image processing arts, a computer program of an exemplary embodiment herein can be utilized by a suitable, general-purpose computer system, such as a personal computer or workstation. However, many other types of computer systems can be used to execute the computer program of described exemplary embodiments, including an arrangement of one or networked processors, for example.

A computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products for exemplary embodiments herein may make use of various image manipulation algorithms and/or processes that are well known. It will be further understood that exemplary computer program product embodiments herein may embody algorithms and/or processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/exemplary embodiments, such feature can be combined with one or more other features of the other implementations/exemplary embodiments as can be desired and advantageous for any given or particular function. The term "a" or "at least one of" is used to mean one or more of the listed items can be selected. The term "about" indicates that the value listed can be somewhat altered, as long as the alteration does not result in nonconformance of the process or structure to the illustrated exemplary embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An intraoral imaging apparatus for tomosynthesis imaging comprising:
   a) an x-ray source having a primary collimator that defines boundaries of a radiation field;
   b) a transport apparatus that translates the x ray source along a path for tomographic imaging;
   c) an intraoral x-ray detector that defines an imaging area for the radiation field;
   d) a positioning apparatus that correlates the position of the intraoral detector to the position of a secondary collimator;
   e) one or more radio-opaque markers provided on a detector attachment that is coupled to the detector, the one or more markers configured to condition acquired x-ray images to relate the spatial position of the intraoral x-ray detector to the x-ray source position, wherein the one or more markers are disposed within the defined imaging area;
   and
   f) a control logic processor that accepts image data from the detector and determines the relative location of the source with respect to the detector according to detected marker position.

2. The apparatus of claim 1 wherein the one or more markers are spherical.

3. The apparatus of claim 1 wherein the one or more markers are formed from radio-opaque materials having atomic numbers not exceeding 45.

4. The apparatus of claim 1 wherein the one or more markers are taken from the group consisting of chromium steel, ceramic, tungsten carbide, and gold.

5. The apparatus of claim 1 wherein the one or more markers are formed of a ceramic.

6. The apparatus of claim 1 wherein the one or more markers are arranged in first and second parallel layers.

7. The apparatus of claim 6 wherein markers on the first parallel layer are formed of a first material and markers on the second parallel layer are formed of a second material and wherein the first and second materials differ in density to radiation.

8. The apparatus of claim 1 wherein the detector attachment couples the intraoral x-ray detector to one or more teeth.

9. The apparatus of claim 1 wherein the one or more markers are encased in plastic.

10. An apparatus for geometric calibration of an intraoral tomosynthesis imaging system, the apparatus comprising:
    an x-ray imaging system that directs x-ray radiation toward an intraoral detector from a plurality of acquisition angles with respect to the detector;
    a holder that positions the detector within the mouth of a patient, wherein the holder disposes radio-opaque markers in the path of the x-ray radiation at each of the plurality of acquisition angles, wherein the holder disposes markers in position along opposite surfaces of at least one tooth;
    and
    a control logic processor that acquires image data from the detector and determines the relative location of the source with respect to the detector according to detected marker positions in the acquired image data.

11. The apparatus of claim 10 wherein the radio-opaque markers are formed from materials having atomic number not exceeding 45.

12. The apparatus of claim 10 wherein the holder clips onto one or more teeth.

13. The apparatus of claim 10 wherein the holder distributes the markers over two parallel planes and the number of markers along one plane differs from the number of markers along the other plane.

14. The apparatus of claim 10 wherein the holder clips onto the detector.

15. A method for geometric calibration of an intraoral tomosynthesis imaging system, the method executed at least in part by a computer and comprising:
    coupling an intraoral detector with a calibration phantom that includes a first set of radio-opaque markers distributed along a first plane and a second set of radio-opaque markers distributed along a second plane;
    positioning the intraoral detector within the mouth of a patient;
    directing x-ray radiation from an x-ray source toward an intraoral detector from a plurality of angles with respect to the detector;
    and
    acquiring image data from the intraoral detector and calculating the relative location of the x-ray source with respect to the detector at each of the plurality of angles, according to detected marker position.

16. The method of claim 15 wherein positioning the intraoral detector within the mouth comprises fitting the calibration phantom onto a tooth of the patient.

17. The method of claim 15 wherein positioning the intraoral detector within the mouth comprises providing a bite surface on a portion of the calibration phantom.

18. A method for geometric calibration of an intraoral tomosynthesis imaging system, the method executed at least in part by a computer and comprising:
    coupling an intraoral detector with a calibration phantom that includes a first set of radio-opaque markers distributed along a first plane and a second set of radio-opaque markers distributed along a second plane;
    positioning the intraoral detector within the mouth of a patient;
    directing x-ray radiation from an x-ray source toward an intraoral detector from a plurality of angles with respect to the detector;
    acquiring image data from the intraoral detector and calculating the relative location of the x-ray source with respect to the detector at each of the plurality of angles, according to detected marker position;
    and
    obtaining one or more depth-resolved images using an ultrasound or optical coherence tomography system and verifying positioning of the acquired image data from the intraoral detector using the one or more depth-resolved images.

19. A method for geometric calibration of an intraoral tomosynthesis imaging system, the method executed at least in part by a computer and comprising:
    coupling an intraoral detector with a calibration phantom that includes a first set of radio-opaque markers distributed along a first plane and a second set of radio-opaque markers distributed along a second plane;
    positioning the intraoral detector within the mouth of a patient;
    directing x-ray radiation from an x-ray source toward an intraoral detector from a plurality of angles with respect to the detector;
    and
    acquiring image data from the intraoral detector and calculating the relative location of the x-ray source with respect to the detector at each of the plurality of angles, according to detected marker position;
    and
    obtaining one or more depth-resolved images using an ultrasound or optical coherence tomography system and reporting patient movement detected during tomosynthesis image data acquisition.

* * * * *